United States Patent [19]
Monia et al.

[11] Patent Number: 6,114,517
[45] Date of Patent: Sep. 5, 2000

[54] METHODS OF MODULATING TUMOR NECROSIS FACTOR α-INDUCED EXPRESSION OF CELL ADHESION MOLECULES

[75] Inventors: Brett P. Monia, La Costa, Calif.; Xiaoxing S. Xu, Maddison, N.J.

[73] Assignee: Isis Pharmaceuticals Inc., Carlsbad, Calif.

[21] Appl. No.: 09/209,668

[22] Filed: Dec. 10, 1998

[51] Int. Cl.[7] .......................... C07H 21/04; C07H 21/02; C12Q 1/68; C12N 15/85; A61K 48/00

[52] U.S. Cl. .................. 536/24.5; 536/23.1; 536/24.3; 435/6; 435/91.1; 435/91.31; 435/375; 514/44

[58] Field of Search .................................. 536/23.1, 24.5, 536/24.31; 435/6, 375, 91.1, 91.31; 514/44

[56] References Cited

U.S. PATENT DOCUMENTS

| | | | |
|---|---|---|---|
| 5,514,778 | 5/1996 | Bennett et al. | 536/23.1 |
| 5,563,255 | 10/1996 | Monia et al. | 536/24.31 |
| 5,576,208 | 11/1996 | Monia et al. | 435/375 |
| 5,582,986 | 12/1996 | Monia et al. | 435/6 |
| 5,591,623 | 1/1997 | Bennett et al. | 435/375 |
| 5,656,212 | 8/1997 | Monia et al. | 514/44 |
| 5,877,309 | 3/1999 | McKay et al. | 536/24.5 |

FOREIGN PATENT DOCUMENTS

WO 92/22651  12/1992  WIPO.

OTHER PUBLICATIONS

Crooke, S., Basic Principles of Antisense Therapeutics, Springer–Verlag Berlin Heidelberg New York, Jul. 1998.

Gura T., Antisense Has Growing Pains, Science, vol. 270, pp. 575–577, Oct. 1995.

Crooke, S. et al., Antisense '97: A roundtable on the state of the industry, Nature Biotechnology, vol. 15, p.522, Jun. 1997.

Branch, A., A good antisense molecule is hard to find, TIBS vol. 23, pp. 47–49, Feb. 1998.

Minden et al., Regulation and function of the JNk subgroup of MAP kinases, Biochimica et Biophysica Acta 1333 (1997), pp. F85–F104.

Min et al. TNF initiates E–selectin transcription . . . , vol. 159, 7, Journal of Immunology, pp. 3508–3518, 1997.

Bost, et al., "The JUN Kinase/Stress–activated Protein Kinase Pathway Is Required for Epidermal Growth Factor Stimulation of Growth of Human A549 Lung Carcinoma Cells", 1997; *J. Biol. Chem.*, 272; 33422–33429.

*Primary Examiner*—George C. Elliott
*Assistant Examiner*—Janet L. Epps
*Attorney, Agent, or Firm*—Law Offices of Jane Massey Licata

[57] ABSTRACT

Methods are provided for inhibiting the expression of cell adhesion molecules using inhibitors of signaling molecules involved in human TNF-α signaling. These inhibitors include monoclonal antibodies, peptide fragments, small molecule inhibitors, and, preferably, antisense oligonucleotides. Methods for treatment of diseases, particularly inflammatory and immune diseases, associated with overexpression of cell adhesion molecules are provided.

8 Claims, 3 Drawing Sheets

METHODS OF MODULATING TUMOR NECROSIS FACTOR α-INDUCED EXPRESSION OF CELL ADHESION MOLECULES

FIELD OF THE INVENTION

The present invention relates to the modulation of expression of cell adhesion molecules. In particular, herein are provided methods of inhibiting cell adhesion molecule gene expression through specific inhibitors involved in TNF-α signaling. Methods are also provided for treating inflammatory and immune diseases associated with altered expression of cell adhesion molecules.

BACKGROUND OF THE INVENTION

Cytokines represent a diverse group of regulatory proteins with numerous biological functions including cell differentiation, cell growth, and cytotoxity. Inflammatory cytokines such as Tumor Necrosis Factor alpha and (TNF-α)and IL-1 (interleukin-1) have been shown to play pivotal roles in immune and inflammatory responses (McIntyre, T. M., et al., Thromb. Haemos. 1997, 78, 302–305). One of the most important effector functions of these cytokines is their ability to induce profound changes in the vascular endothelium (Introna, M. and Mantovani, A., Art. Thromb. and Vasc. Biol. 1997, 17, 423–428). Central to the process of inflammation is the induction of cell adhesion molecules on the endothelial cell surface, contributing significantly to the adherence and recruitment of circulating leukocytes to inflammatory sites. Upon exposure to TNF-α or IL-1, which are produced in response to injury or infection, cytokine receptors on endothelial cells activate a variety of intracellular signaling molecules. These signaling events result in the activation of specific transcription factors such as NF-kB and upregulate the expression of E-selectin, ICAM-1, VCAM-1, and other cell adhesion molecules (McIntyre, T. M., et al., Thromb. Haemos. 997, 78, 302–305; Introna, M. and Mantovani, A., Art. Thromb. and Vasc. Biol. 1997, 17, 423–428; Mantovani, A., et al., Thromb. Haemos. 1997, 78, 406–414). E-selectin has been shown to mediate the initial attachment and rolling of leukocytes along the vessel wall, whereas ICAM-1 and VCAM-1 are involved in the firm adhesion of leukocytes to the vessel wall and their transmigration through the vessel wall. E-selectin is rapidly and transiently induced by cytokines with peak expression occurring approximately 4–6 hours after exposure and returning to basal levels approximately 24 hours post exposure. In contrast, induction of ICAM-1 and VCAM-1 by cytokines is slower and persists for 24 hours or longer (Mantovani, A., et al., Thromb. Haemos. 1997, 78, 406–414; Dunon, D., et al., Curr. Opin. Cell Bio, 1996, 8, 714–723; Bischoff, J., Cell Adhes. and Angiog., 1997, 99, 373–376).

Responses to TNF-α are mediated through interactions with two distinct membrane receptors, termed TNFRI (TNF-α receptor I) and TNFRII (TNF-α receptor II). Two distinct families of adaptor proteins associated with TNF-α receptors have been identified. The death domain-containing proteins (e.g., TRADD) appear to couple the receptors to programmed cell death (Fiers, W., et al., J. Inflam., 1996, 47, 67–75; Wallach, D., et al., FEBS Lett., 1997, 410, 96–106; Hsu, H., et al., Cell, 1996, 84, 299–308), whereas the TRAF (TNF receptor associated factor) domain-containing proteins link the receptors to activation of specific transcription factors (Hsu, H., et al., Cell, 1996, 84, 299–308; Baeuerle, P. A., Curr. Biol., 1998, 8, R19–R22). Among the six members of the TRAF family that have been identified so far, TRAF2 has been reported to be important for TNF-α-mediated activation of JNK (c-Jun N-terminal kinase), as well as two major transcription factors, NF-kB (nuclear factor-kB) and AP-1 (activator protein 1) (Hsu, H., et al., Cell, 1996, 84, 299–308; Baeuerle, P. A., Curr. Biol., 1998, 8, R19–R22; Natoli, G., et al., J. Biol. Chem., 1997, 272, 26079–26082; Liu, Z. G., et al., Cell, 1996, 87, 565–576; Song, H. Y., et al., Proc. Natl. Acad. Sci. USA, 1997, 94, 9792–9796). Both transcription factors play pivotal roles in the regulation of multiple genes including those involved in immune and inflammatory responses. AP-1 is activated by various MAPKs (mitogen-activated protein kinase) including ERK (extracellular-signal-regulated kinase), JNK and p38 MAPK (Fiers, W., et al., J. Inflam., 1996, 47, 67–75; Eder, J., TIPS, 1997, 18, 319–322). NF-kB is constitutively present in the cytosol of endothelial cells and kept inactive by association with inhibitory IkB family proteins. Upon exposure to TNF-α, IKK (IkB kinase) phosphorylates IkB and initiates its ubiquitination and subsequent degradation. The released NF-kB translocates to the nucleus and participates in transcriptional activation (Collins, T., et al., FASEB J., 1995, 9, 899–909; Stancovski, I., and Baltimore, D., Cell, 1997, 91, 299–302).

Other signaling molecules, including MEKK1, pp90rsk (ribosomal S6 protein kinase), ras, and raf, have been implicated in the activation of NF-kB (Schulze-Osthoff, K., et al., Immunobiol., 1997, 198, 35–49). ras family members (Ha-ras, Ki-ras, N-ras) are GTP-binding proteins that act as major mediators in the regulation of cell proliferation and differentiation in response to a variety of extracellular stimuli including TNF-α (Bos, J. L., Biochem. Biophys. Acta, 1997, 1333, M19–M31). ras proteins have been shown to activate both the raf/MEK/ERK pathway as well as MEKK/JNKK/JNK pathway (Bos, J. L., Biochem. Biophys. Acta, 1997, 1333, M19-M31; Marais, R., and Marshall, C. J., Cancer Surveys, 1996, 27, 101–125; Adler, V., et al., J. Biol. Chem., 1996, 271, 23304–23309; Faris, M., et al., J. Biol. Chem., 1996, 271, 27366–27373; Terada, K., et al., J. Biol. Chem., 1997, 272, 4544–4548). raf family members (A-, B-, c-raf) are serine/threonine protein kinases that transmit signals from cell surface receptors to a variety of intracellular effectors including the MAPK pathways (Marais, R., and Marshall, C. J., Cancer Surveys, 1996, 27, 101–125; Daum, G., et al., TIBS, 1994, 19, 474–480). Besides ras, a variety of protein kinases including Src family kinases and PKC (protein kinase C) can potentiate raf activity (Marais, R., et al., J. Biol. Chem., 1997, 272, 4378–4383; Ueffing, M., et al., Oncogene, 1997, 15, 2921–2927). The major downstream effectors of raf are MEK/MKK1 (MAP kinase kinase 1) and MEK/MKK2 (MAP kinase kinase 2) which in turn phosphorylate and activate ERK1/2, and ultimately activate specific transcription factors (Marais, R., and Marshall, C. J., Cancer Surveys, 1996, 27, 101–125; Daum, G., et al., TIBS, 1994, 19, 474–480). Both ras and raf had been suggested to participate in the activation of NF-kB transcription factors (Schulze-Osthoff, K., et al., Immunobiol., 1997, 198, 35–49; Folgueira, L., et al., J. Virol., 1996, 70, 2332–2338; Koong, A. C., et al., Cancer Res., 1994, 54, 5273–5279; Bertrand, F., et al., J. Biol. Chem., 1995, 270, 24435–24441; Kanno, T., and Siebenlist, U., J. Immunol., 1996, 157, 5277–5283).

In many human diseases with an inflammatory component, the normal, homeostatic mechanisms which attenuate the inflammatory responses are defective, resulting in damage and destruction of normal tissue. For example, VCAM-1 may play a role in the metastasis of melanoma, and possibly other cancers. In addition, data have demonstrated that ICAM-1 is the cellular receptor for the major serotype of rhinovirus, which account for greater than 50% of common colds. (Staunton, et al., Cell, 1989, 56, 849–853; Greve et al., Cell, 1989, 56, 839–847).

Expression of ICAM-1 has also been associated with a variety of inflammatory skin disorders such as allergic contact dermatitis, fixed drug eruption, lichen planus, and psoriasis (Ho, et al., J. Am. Acad. Dermatol., 1990, 22, 64–68; Griffiths and Nickoloff, Am. J. Pathology, 1989, 135, 1045–1053; Lisby, et al., Br. J. Dermatol., 1989, 120, 479–484; Shiohara, et al., Arch. Dermatol., 1989, 125, 1371–1376). In addition, ICAM-1 expression has been detected in the synovium of patients with rheumatoid arthritis (Hale, et al., Arth. Rheum., 1989, 32, 22–30), pancreatic B-cells in diabetes (Campbell, et al., Proc. Natl. Acad. Sci. U.S.A., 1989, 86, 4282–4286), thyroid follicular cells in patients with Graves' disease (Weetman, et al., J. Endocrinol., 1989, 122, 185–191), and with renal and liver allograft rejection (Faull and Russ, Transplantation, 1989, 48, 226–230; Adams, et al., Lancet, 1989, 2, 1122–1125).

Inhibitors of ICAM-1, VCAM-1 and ELAM-1 expression would provide a novel therapeutic class of anti-inflammatory agents with activity towards a variety of inflammatory diseases or diseases with an inflammatory component such as asthma, rheumatoid arthritis, allograft rejections, inflammatory bowel disease, various dermatological conditions, and psoriasis. In addition, inhibitors of ICAM-1, VCAM-1, and ELAM-1 may also be effective in the treatment of colds due to rhinovirus infection, AIDS, Kaposi's sarcoma and some cancers and their metastasis. The use of neutralizing monoclonal antibodies against ICAM-1 in animal models provide evidence that such inhibitors if identified would have therapeutic benefit for asthma (Wegner, et al., Science, 1990, 247, 456–459), renal allografts (Cosimi, et al., J. Immunol., 1990, 144, 4604–4612), and cardiac allografts (Isobe, et al., Science, 1992, 255, 1125–1127). The use of a soluble form of ICAM-1 molecule was also effective in preventing rhinovirus infection of cells in culture (Marlin, et al., Nature, 1990, 344, 70–72).

Current agents which affect intercellular adhesion molecules include synthetic peptides, monoclonal antibodies, soluble forms of the adhesion molecules, and antisense oligonucleotides. Antisense oligonucleotides to cell adhesion molecules are disclosed in U.S. Pat. Nos. 5,514,788 and 5,591,623, herein incorporated by reference. These have been directed against a single cell adhesion molecule. Additional agents are desired. Furthermore, a broader approach, targeting several adhesion molecules with a single agent may have several advantages, including economies of scale, broad spectrum utility, etc. Thus, an approach to target a molecule in the TNF-α signaling pathway may be a useful therapeutic treatment, providing a means to regulate multiple cell adhesion molecules with a single agent.

Inhibitors of molecules in TNF-α mediated signaling have been used to study the signal transduction pathways and suggest utility in the design of pharmacological agents. Inhibitors that have been used include DMSO (Essani, N. A., et al., Shock, 1997, 7, 90–96) against NF-kB, protein tyrosine kinase inhibitors (Adamson, P., et al., Cell Adhes. Commun.,1996, 3, 511–525; Pai, R., et al., J. Immunol., 1996, 156, 2571–2579), protein tyrosine kinase C inhibitors (Ballestas, M. E. and Benveniste, E. N., Glia, 1995, 14, 267–278), ubiquitin ligase inhibitors (Yaron, A., et al., EMBO J., 1997, 16, 6486–6494), and phospholipase A2 inhibitors (Thommesen, L., et al., J. Immunol., 1998, 161, 3421–3430). In addition, drugs that elevate cyclic AMP have been found to inhibit ELAM-1 and VCAM-1 (Pober, J. S., et al., J. Immunol., 1993, 150, 5114–5123).

Antisense oligonucleotides to c-raf, Ha-ras and JNK2 are known, but have not previously been shown to inhibit cell adhesion molecule expression. The relationship between these TNF-α signaling molecules and cell adhesion molecule expression has not been fully delineated. c-raf antisense oligonucleotides are disclosed in U.S. Pat. Nos. 5,563,255 and 5,656,612, herein incorporated by reference. Ha-ras antisense oligonucleotide are disclosed in U.S. Pat. Nos. 5,576,208 and 5,582,986, herein incorporated by reference. JNK2 antisense oligonucleotides are disclosed by Bost, F., et al. (J. Biol. Chem. 1997, 272, 33422–33429). Inhibitors of the TNF-α signaling molecules, c-raf, Ha-ras and JNK2 have not been used to modulate expression of cell adhesion molecules and represent a novel approach.

BRIEF DESCRIPTION OF THE INVENTION

Figure 1:
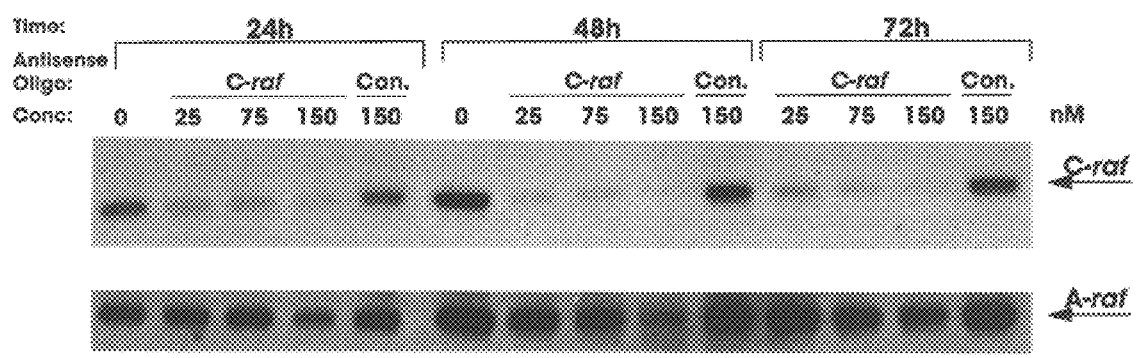
FIG. 1 is a Western blot showing a time-course of the effects of c-raf antisense oligonucleotides on c-raf and a-raf protein levels.

The present invention describes a method of modulating cell adhesion molecule expression within a cell comprising treating said cell with a specific inhibitor of one of the Tumor Necrosis Factor alpha (TNF-α) signaling molecules, Ha-ras, c-raf or JNK2. In one embodiment, the specific inhibitor is an antisense oligonucleotide capable of hybridizing to Ha-ras, c-raf or JNK2. Also provided are methods of treating an inflammatory or immune disease or condition associated with altered expression of a cell adhesion molecule comprising administering a specific inhibitor of one of the TNF-α signaling molecules, Ha-ras, c-raf or JNK2.

DETAILED DESCRIPTION OF THE INVENTION

The present invention employs specific inhibitors of Ha-ras, c-raf and JNK2, members of the TNF-α signaling pathway, to modulate cell adhesion molecule expression. These inhibitors can include monoclonal antibodies, peptide fragments, small molecule inhibitors and antisense compounds. In a preferred embodiment, antisense compounds, particularly oligonucleotides, are used to modulate the function of nucleic acid molecules encoding Ha-ras, c-raf or JNK2, modulating the amount of protein produced and ultimately modulating the expression of cell adhesion molecules. This is accomplished by providing oligonucleotides which specifically hybridize with nucleic acids, preferably mRNA, encoding Ha-ras, c-raf or JNK2.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding Ha-ras, c-raf or JNK2; in other words, a gene encoding Ha-ras, c-raf or JNK2, or mRNA expressed from the Ha-ras, c-raf or JNK2 gene. mRNA which encodes Ha-ras, c-raf or JNK2 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Ha-ras, c-raf or JNK2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon—exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of c-raf, Ha-ras or JNK2 and, in the context of this invention, ultimately modulation of cellular adhesion molecule expression. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The oligonucleotides of this invention can be used in diagnostics, therapeutics, prophylaxis, and as research reagents and in kits. Since the oligonucleotides of this invention hybridize to nucleic acids encoding Ha-ras, c-raf or JNK2, sandwich, calorimetric and other assays can easily be constructed to exploit this fact. Provision of means for detecting hybridization of oligonucleotide with the Ha-ras, c-raf or JNK2 gene or mRNA can routinely be accomplished. Such provision may include enzyme conjugation, radiolabelling or any other suitable detection systems. Kits for detecting the presence or absence of Ha-ras, c-raf or JNK2 may also be prepared.

The present invention is also suitable for diagnosing abnormal inflammatory states in tissue or other samples from patients suspected of having an inflammatory disease such as rheumatoid arthritis. The ability of the oligonucleotides of the present invention to inhibit inflammatory processes may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide (s), usually in a liquid carrier, to a cell suspension or tissue sample, either in vitro or ex vivo, or to administer the oligonucleotide(s) to cells or tissues within an animal.

The oligonucleotides of this invention may also be used for research purposes. For example, the function of a specific gene product in a signaling pathway may be investigated using specific oligonucleotides. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (Science, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are [($CH_2$)$_n$O]$_m$$CH_3$, O($CH_2$)$_n$O$CH_3$, O($CH_2$)$_2$ON($CH_3$)$_2$, O($C_2$)$_n$N$H_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O-$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow.

Other preferred modifications include 2'-methoxy (2'-O-$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, 1990, pages 858–859, Kroschwitz, J. I., ed. John Wiley & Sons, those disclosed by Englisch et al. (Angewandte Chemie, International Edition, 1991, 30, 613–722), and those disclosed by Sanghvi, Y. S., Chapter 15, Antisense Research and Applications, 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553–6556), cholic acid (Manoharan et al., Bioorg. Med. Chem. Lett., 1994, 4, 1053–1059), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantane acetic acid (Manoharan et al., Tetrahedron Lett., 1995, 36, 3651–3654), a palmityl moiety (Mishra et al., Biochim. Biophys. Acta., 1995, 1264, 229–237), or an octadecylamine or hexylamino-carbonyl-oxycholesterol moiety (Crooke et al., J. Pharmacol. Exp. Ther., 1996, 277, 923–937).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl- substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$)_2 modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta, 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci., 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems, 1991, 8, 91–192; Muranishi, Critical Reviews in Therapeutic Drug Carrier Systems, 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems, 1991, page 92; Muranishi, Critical Reviews in Therapeutic Drug Carrier Systems, 1990, 7, 1; El-Hariri et al., J. Pharm. Pharmacol., 1992 44, 651–654).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems, 1991, page 92; Muranishi, Critical Reviews in Therapeutic Drug Carrier Systems, 1990, 7, 1–33; Buur et al., J. Control Rel., 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorochemical emulsions, such as FC-43 (Takahashi et al., J. Pharm. Phamacol., 1988, 40, 252–257).

Non-surfactants include, for example, unsaturated cyclic ureas, 1-alkyl- and 1-alkenylazacyclo-alkanone derivatives (Lee et al., Critical Reviews in Therapeutic Drug Carrier Systems 1991, page 92); and non-steroidal anti-inflammatory agents such as diclofenac sodium, indomethacin and phenylbutazone (Yamashita et al., J. Pharm. Pharmacol., 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech., 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed., 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1: Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (J. Med. Chem., 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (Helv. Chim. Acta, 1995, 78, 486–506). For ease of synthesis, the last nucleotide may be a deoxynucleotide. 2'-O—$CH_2CH_2OCH_3$-cytosines may be 5-methyl cytosines. Synthesis of 5-Methyl cytosine monomers:

2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% Et $N_3H$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite:

$N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., Nucl. Acids Res., 1993, 21, 3197–3203) using commercially available phosphoramidites (Glen Research, Sterling Va. or ChemGenes, Needham Mass.).

2'-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at –10° C. to 0° C. After 1 hr the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy) ethyl]-5-methyluridine as white foam (1.95, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in CH$_2$Cl$_2$). Aqueous NaHCO$_3$ solution (5%, 10 mL) was added and extracted with ethyl acetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylaminooxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (Acc. Chem. Res., 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (Science, 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (J. Biol. Chem., 1991, 266, 18162). Results obtained with HPLC-purified material were similar to those obtained with non-HPLC purified material.

Example 2: Oligonucleotide Sequences and Cell Culture

Antisense oligonucleotides were designed to E-selectin, Ha-ras, c-raf, JNK1, and JNK2. Additional sequences were designed as scrambled controls. The sequence of the oligonucleotides used are given in Table 1. All of these oligonucleotides except ISIS 11928 (SEQ ID NO. 1) contain 2'-O-methoxyethyl/phosphodiester residues flanking a 2'-deoxynucleotide/phosphorothioate region. ISIS 11928 (SEQ ID No. 1) is a fully phosphorothioated oligonucleotide with all 2'-methoxyethoxy nucleotides, except for a 3' terminal 2'-deoxy nucleotide. The target sequence for E-selectin was obtained from the Genbank endothelial leukocyte adhesion molecule I exon 1 sequence, HUMELAM1 (Accession number M61895; SEQ ID NO. 8). The target sequence for Ha-ras was obtained from the Genbank Ha-ras sequence, HSRAS1 (Accession number V00574; SEQ ID NO. 10). The target sequence for c-raf was obtained from the Genbank c-raf sequence, HSRAFR (Accession number X03484; SEQ ID NO. 12). The target sequence for JNK1 was obtained from the Genbank JNK1 sequence, HUMJNK1 (Accession number L26318; SEQ ID NO. 14). The target sequence for JNK2 was obtained from the Genbank JNK2 sequence, HUMJNK2 (Accession number L31951; SEQ ID NO. 16).

TABLE 1

Nucleotide Sequences of Mixed Backbone Chimeric (deoxy gapped) 2'-O-methoxyethyl Oligonucleotides

| ISIS NO. | NUCLEOTIDE SEQUENCE (5' -> 3')[1] | SEQ ID NO: | TARGET GENE |
|---|---|---|---|
| 11928 | GsAsAsGsTsCsAsGsCsCsAsAsGsAsAsCsAsGsCsT | 1 | E-selectin |
| 12854 | ToCoCoCoGoCsCsTsGsTsGsAsCsAsToGoCoAoToT | 2 | c-raf |
| 15727 | AoToGoCoAoTsTsCsTsGsCsCsCsCsCoAoAoGoGoA | 3 | 12854 control |
| 15168 | ToCoCsGsTsCsAsTsCsGsCsTsCoCoToCoAoGoGoG | 4 | Ha-ras |
| 17552 | ToCoAsGsTsAsAsTsAsGsCsCsCoCoAoCoAoToGoG | 5 | 15168 Control |
| 15347 | CoToCoToCoTsGsTsAsGsGsCsCsCsGsCoToToGoG | 6 | JNK1 |
| 15354 | GoToCoCoGoGsGsCsCsAsGsGsCsCsAsAoAoGoToC | 7 | JNK2 |

[1]Underlined residues are 2'-methoxyethoxy residues (others are 2'-deoxy-). All 2'-methoxyethoxy cytidines are 5-methyl-cytidines; "s" linkages are phosphorothioate linkages, "o" linkages are phosphodiester linkages.

Human dermal microvascular cells (HMVEC-d; Clonetics, San Diego, Calif.) were cultivated in endothelial basal media (EBM, Clonetics) supplemented with 10% fetal bovine serum (HyClone, Logan, Utah). Cells were grown in 100 mm petri dishes until 70–80% confluent, then washed with PBS and OPTI-MEM (Life Technologies, Inc., Gaithersburg, Md.). The cells were then incubated in the presence of OPTI-MEM and 3 mg/ml LIPOFECTIN (a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water (Life Technologies, Gaithersburg, Md.), per 100 nM of oligonucleotide followed by addition of oligonucleotide at the appropriate concentrations.

For determination of mRNA levels by Northern blot, total RNA was prepared from cells by the guanidinium isothiocyanate procedure or by the Qiagen RNAEASY method (Qiagen, Santa Clarita, Calif.) at the indicated times after initiation of oligonucleotide treatment. Northern blot analysis was performed as described in Current Protocols in Molecular Biology (Ausubel, F. M., et al., (eds), 1987, Greene Publishing Assoc. and Wiley Interscience, New York). A glyceraldehyde 3-phosphate dehydrogenase (G3PDH) probe was purchased from Clontech (Palo Alto, Calif., Catalog Number 9805-1). RNA was quantified and normalized to G3PDH mRNA levels using a Molecular Dynamic PHOSPHORIMAGER (Sunnyvale, Calif.).

For determination of protein levels by Western blot, cellular extracts were prepared using 300 ml of RIPA extraction buffer per 100-mm dish. The protein concentration was quantified by Bradford assay using the BioRad kit (BioRad, Hercules, Calif.). Equal amounts of protein were loaded on 10% or 12% SDS-PAGE mini-gel (Novex, San Diego, Calif.). Once transferred to PVDF membranes (Millipore, Bedford, Mass.), the membranes were then treated for a minimum of 2 hours with specific primary antibody followed by incubation with secondary antibody conjugated to HRP. The results were visualized by Enhanced Chemiluminescent (ECL) detection (New England BioLab, Beverly, Mass.). In some experiments, the blots were stripped in stripping buffer (2% SDS, 12.5 mM Tris, pH 6.8) for 30 minutes at 50° C. After extensive washing, the blots were blocked and blotted with different primary antibody.

Example 3: Inhibition of c-raf and Ha-ras Expression by Antisense Oligonucleotides ISIS 12854 (SEQ ID NO. 2) is a 2'-O-methoxyethyl mixed backbone chimeric antisense oligonucleotide designed to hybridize with 3'-untranslated sequences contained within human c-raf mRNA. To determine whether this antisense oligonucleotide is effective as a c-raf inhibitor in endothelial cells, human dermal microvascular cells (HMVEC) were treated with ISIS 12854 (SEQ ID NO. 2) as described in Example 2. C-raf mRNA and protein expression was examined by northern and Western blot analysis. The c-raf cDNA probe was generated from the plasmid, p627 (American Type Culture Collection, Manassas, Va.; catalog #41050), following the supplied instructions. The c-raf antibody was obtained from Transduction Laboratories, Inc. (Lexington, Ky.). Northern blot results are shown in Table 2. Western blot results are shown in FIG. 1.

TABLE 2

Dose Response of ISIS 12854 on c-raf mRNA Levels in HMVEC Cells

| ISIS # | SEQ ID NO: | ASO Gene Target | Dose | % mRNA Expression | % mRNA Inhibition |
|---|---|---|---|---|---|
| LIPOFECTIN | — | — | — | 100% | — |
| 15727 | 3 | control | 100 nM | 96% | 4% |
| " | " | " | 200 nM | 135% | — |
| 12854 | 2 | c-raf | 0.5 nM | 67% | 33% |
| " | " | " | 2.5 nM | 31% | 69% |
| " | " | " | 10 nM | 15% | 85% |
| " | " | " | 50 nM | 10% | 90% |
| " | " | " | 100 nM | 13% | 87% |
| " | " | " | 200 nM | 3% | 97% |

Treatment of HMVEC with ISIS 12854 (SEQ ID NO. 2) resulted in dramatically reduced c-raf mRNA levels. Reduction of c-raf mRNA levels was dose-dependent in the range of 0.5 to 200 nM. The $IC_{50}$ for c-raf mRNA reduction was approximately 2.5 nM. The control oligonucleotide, ISIS 15727 (SEQ ID NO. 3) did not exhibit any effect on c-raf mRNA.

Reduction of c-raf protein levels also occurred following oligonucleotide treatment. Reduction in protein expression was first detectable 24 hours after treatment and maximal reduction of c-raf protein levels was achieved 48 hours after treatment with 150 nM oligonucleotide. Reduction of c-raf protein levels persisted up to 72 hour following initial treatment. Inhibition of c-raf expression by ISIS 12854 (SEQ ID NO. 2) was specific since A-raf protein expression was largely unaffected when the same blot was stripped and blotted with antibody against A-raf (Transduction Laboratories, Inc., Lexington, Ky.).

ISIS 15168 (SEQ ID NO. 4) is a 2'-O-methoxyethyl mixed backbone chimeric antisense oligonucleotide designed to hybridize with sequences contained within the human Ha-ras mRNA. To determine the effect of ISIS 15168 (SEQ ID NO. 4) on Ha-ras expression in endothelial cells, HMVEC were treated, as described in Example 2, with oligonucleotide and northern blotting was used to measure Ha-ras mRNA levels. A Ha-ras probe was generated from the plasmid, pbc-N1 (American Type Culture Collection, Manassas, Va.; catalog #41001), following the supplied instructions. Results are shown in Table 3.

TABLE 3

Dose Response of Ha-ras Antisense Oligodeoxynucleotides on Ha-ras mRNA Levels in HMVEC Cells

| ISIS # | SEQ ID NO: | ASO Gene Target | Dose | % mRNA Expression | % mRNA Inhibition |
|---|---|---|---|---|---|
| LIPOFECTIN ™ | — | — | — | 100% | — |
| 15168 | 4 | Ha-ras | 1 nM | 61% | 39% |
| " | " | " | 5 nM | 44% | 56% |
| " | " | " | 25 nM | 19% | 81% |
| " | " | " | 50 nM | 10% | 90% |
| " | " | " | 100 nM | 9% | 91% |
| 17552 | 5 | control | 1 nM | 103% | — |
| " | " | " | 5 nM | 115% | — |
| " | " | " | 25 nM | 96% | 4% |
| " | " | " | 50 nM | 109% | — |
| " | " | " | 100 nM | 105% | — |

Reduction of Ha-ras mRNA levels in HMVEC was observed following oligonucleotide treatment and was found to be sequence-specific, and dose-dependent ($IC_{50}$<5 nM).

Figure 2:
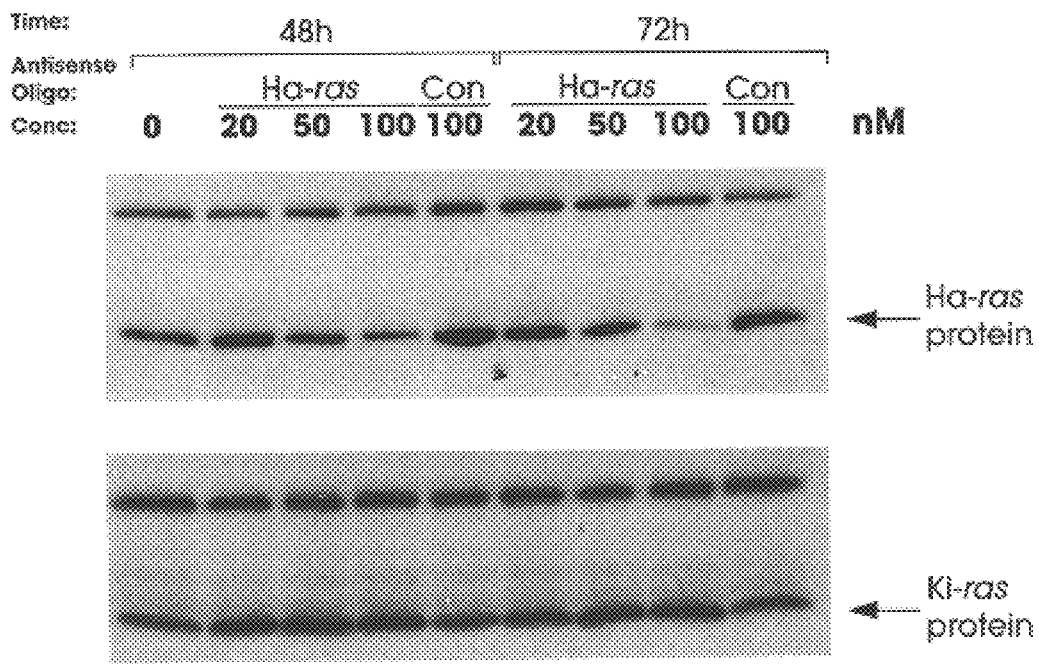
FIG. 2 is a Western blot showing a time-course of the effects of Ha-ras antisense oligonucleotides on Ha-ras and Ki-ras protein levels.

To examine the effect of ISIS 15168 (SEQ ID NO. 4) on Ha-ras protein levels, total ras protein was immunoprecipitated using a pan-ras monoclonal antibody (Oncogene Science, Cambridge, Mass.). The precipitated proteins were analyzed by SDS-PAGE, and Ha-ras protein levels were determined by western blot using a monoclonal antibody specific for Ha-ras (Oncogene Science, Cambridge, Mass.). As shown in FIG. 2, dose-dependent reduction of Ha-ras protein expression was observed 48 hours following treatment with ISIS 15168 (SEQ ID NO. 4) This reduction persisted up to 72 hours following initial treatment. The kinetics of Ha-ras reduction was slower than that of c-raf. The control oligonucleotide, ISIS 17552 (SEQ ID NO. 5), had no effect on Ha-ras protein level. The same blot was stripped and blotted a second time with a Ki-ras-specific antibody (Oncogene Science, Cambridge, Mass.). No effect on Ki-ras protein levels was observed in cells treated with either ISIS 15168 (SEQ ID NO. 4) or the control oligonucleotide, ISIS 17552 (SEQ ID NO. 5).

Example 4: Effect of inhibiting c-raf and Ha-ras Gene Expression on the Induction of E-selectin The effect of c-raf and Ha-ras antisense oligonucleotide treatment on the induction of E-selectin by TNF-α was examined. HMVEC cells were treated with either the c-raf or Ha-ras antisense compound under dose-response conditions or over time at a single dose level followed by stimulation of E-selectin expression by TNF-α for 5 hours. The cell surface expression of E-selectin was determined by flow cytometry analysis. Following oligonucleotide treatment, cells were detached from the plates and analyzed for surface expression of cell adhesion molecules using a Becton Dickinson (San Jose, Calif.) FACScan. TNF-α and FITC conjugated antibody for E-selectin were obtained from R & D Systems (Minneapolis, Minn.). PE-conjugated antibody for ICAM-1 was obtained from Pharmingen (San Diego, Calif.). VCAM-1 antibody was obtained from Santa Cruz Biotechnology, Santa Cruz, Calif. Cell surface expression was calculated using the mean value of fluorescence intensity using 3,000–5,000 cells stained with the appropriate antibody for each sample and time point. Results are expressed as percentage of control (cell surface expression induced by TNF-α in cells that were not treated with oligonucleotides) based upon mean fluorescence intensity. Results are shown in Tables 4 and 5. Basal expression of E-selectin and VCAM-1 is undetectable in the absence of TNF-α whereas a low level of basal expression is detectable for ICAM-1.

TABLE 4

Dose Response of the effect of c-raf and Ha-ras Antisense Oligonucleotides in Induction of E-selectin

| ISIS # | SEQ ID NO: | ASO Gene Target | Dose | % Cell Surface Expression | % Cell Surface Inhibition |
|---|---|---|---|---|---|
| LIPOFECTIN ™ | — | — | — | 100% | — |
| 12854 | 2 | c-raf | 25 nM | 37% | 63% |
| " | " | " | 75 nM | 26% | 74% |
| " | " | " | 150 nM | 23% | 77% |
| 15727 | 3 | control | 25 nM | 119% | — |
| " | " | " | 75 nM | 94% | 6% |
| " | " | " | 150 nM | 106% | — |
| 15168 | 4 | Ha-ras | 25 nM | 72% | 28% |
| " | " | " | 75 nM | 47% | 53% |
| " | " | " | 150 nM | 41% | 59% |
| 17552 | 5 | control | 25 nM | 134% | — |
| " | " | " | 75 nM | 116% | — |
| " | " | " | 150 nM | 116% | — |

Dose-dependent inhibition of E-selectin cell surface expression was observed in cells treated with both antisense compounds, ISIS 12854 (SEQ ID NO. 2), targeted to c-raf and ISIS 15168 (SEQ ID NO. 4) targeted to Ha-ras. Maximal inhibition of E-selectin induction was approximately 80% for ISIS 12854 (SEQ ID NO. 2) and 60% for ISIS 15168 (SEQ ID NO. 4). Control oligonucleotides (SEQ ID NO. 3 and SEQ ID NO. 5) exhibited little to no effect on E-selectin induction. These results indicate that reduction of c-raf or Ha-ras protein levels blocked the induction of E-selectin by TNF-α in HMVEC.

The effects of c-raf, Ha-ras, and a E-selectin antisense oligonucleotide on TNF-α-induced E-selectin cell surface expression under kinetic conditions were examined. If the inhibition of E-selectin induction by the c-raf and Ha-ras antisense compounds was dependent on the reduction of c-raf and Ha-ras protein levels, the kinetics of inhibition of E-selectin induction by the antisense compounds should correlate with suppression of c-raf and Ha-ras protein levels (which is dependent on the half-lives of the proteins in cells). Inhibition of E-selectin induction using the E-selectin antisense oligonucleotide should occur much more quickly since this inhibitor blocks E-selectin induction directly. To test this, cells were treated, separately, with antisense oligonucleotides to E-selectin, ICAM-1 and VCAM-1 and allowed to recover prior to TNF-α treatment. TNF-α was added at different time points between 12 and 72 hours following oligonucleotide treatment. E-selectin cell surface expression was measured by flow cytometry analysis after 5 hours of TNF-A treatment. Results are shown in Table 5.

TABLE 5

Time Course of the Effect of c-raf and Ha-ras Antisense Oligonucleotides in Induction of E-selectin

| ISIS # | SEQ ID NO: | ASO Gene Target | Time (hours) | % Cell Surface Expression | % Cell Surface Inhibition |
|---|---|---|---|---|---|
| LIPOFECTIN | — | — | — | 100% | — |
| 11928 | 1 | E-selectin | 12 h/20 h | 22% | 78% |
| " | " | " | 48 h | 29% | 71% |
| " | " | " | 72 h | 32% | 68% |
| 12854 | 2 | c-raf | 12 h/20 h | 58% | 42% |
| " | " | " | 48 h | 23% | 77% |
| " | " | " | 72 h | 24% | 76% |
| 15727 | 3 | control | 12 h/20 h | 93% | 7% |
| " | " | " | 48 h | 106% | — |
| " | " | " | 72 h | 81% | 19% |
| 15168 | 4 | Ha-ras | 12 h/20 h | 87% | 13% |
| " | " | " | 48 h | 42% | 58% |
| " | " | " | 72 h | 42% | 58% |
| 17552 | 5 | control | 12 h/20 h | 113% | — |
| " | " | " | 48 h | 116% | — |
| " | " | " | 72 h | 111% | — |

Concentrations as low as 20 nM of the E-selectin oligonucleotide, ISIS 11928 (SEQ ID NO. 1) were found to block 80% of E-selectin cell surface expression 12 hours following treatment. In contrast, maximal inhibition of E-selectin induction by c-raf and Ha-ras antisense compounds, SEQ ID NO. 2 and SEQ ID NO. 4, respectively, was observed 48 hours following antisense treatment. Some inhibition of E-selectin induction was observed at 12 hours following treatment, but this inhibition was clearly not maximal. These results strongly suggest that inhibition of E-selectin induction by TNF-α in HMVEC following treatment with c-raf and Ha-ras antisense oligonucleotides is a consequence of reduced c-raf and Ha-ras protein levels.

Example 5: Effect of c-raf and Ha-ras Antisense Oligonucleotides on the Induction of other Cell Adhesion Molecules TNF-α induction of ICAM-1 and VCAM-1 in cells treated with c-raf and Ha-ras antisense oligonucleotides was also examined to further define the roles of c-raf and Ha-ras in cytokine signaling. Oligonucleotides were tested, using flow cytometry analysis, as described in Example 4. Results are shown in Table 6 (ICAM-1) and Table 7 (VCAM-1).

TABLE 6

Dose response of the effect of c-raf and Ha-ras antisense oligonucleotides in induction of ICAM-1

| ISIS # | SEQ ID NO: | ASO Gene Target | Dose (conc.) | % Cell Surface Expression | % Cell Surface Inhibition |
|---|---|---|---|---|---|
| LIPOFECTIN ™ | — | — | — | 100% | — |
| 12854 | 2 | c-raf | 20 nM | 80% | 20% |

TABLE 6-continued

Dose response of the effect of c-raf and Ha-ras antisense oligonucleotides in induction of ICAM-1

| ISIS # | SEQ ID NO: | ASO Gene Target | Dose (conc.) | % Cell Surface Expression | % Cell Surface Inhibition |
|---|---|---|---|---|---|
| " | " | " | 50 nM | 62% | 38% |
| " | " | " | 100 nM | 57% | 43% |
| 15727 | 3 | control | 20 nM | 97% | 3% |
| " | " | " | 50 nM | 89% | 11% |
| " | " | " | 100 nM | 87% | 13% |
| 15168 | 4 | Ha-ras | 20 nM | 81% | 19% |
| " | " | " | 50 nM | 62% | 38% |
| " | " | " | 100 nM | 54% | 46% |
| 17552 | 5 | control | 20 nM | 102% | — |
| " | " | " | 50 nM | 100% | — |
| " | " | " | 100 nM | 98% | 2% |

Induction of ICAM-1 by TNF-α was also blocked by c-raf (ISIS 12854, SEQ ID NO. 2) and Ha-ras (ISIS 15168, SEQ ID NO. 4) antisense oligonucleotides, with maximal inhibition greater than 40%.

Treatment of cells with c-raf and Ha-ras antisense oligonucleotides inhibited VCAM-1 expression in a dose-dependent fashion as well. Results are shown in Table 7.

TABLE 7

Dose response of the effect of c-raf and Ha-ras antisense oligonucleotides in induction of VCAM-1

| ISIS # | SEQ ID NO: | ASO Gene Target | Dose (conc.) | % Cell Surface Expression | % Cell Surface Inhibition |
|---|---|---|---|---|---|
| LIPOFECTIN ™ | — | — | — | 100% | — |
| 12854 | 2 | c-raf | 20 nM | 46% | 54% |
| " | " | " | 50 nM | 37% | 63% |
| " | " | " | 100 nM | 28% | 72% |
| 15727 | 3 | control | 20 nM | 69% | 31% |
| " | " | " | 50 nM | 81% | 19% |
| " | " | " | 100 nM | 74% | 26% |
| 15168 | 4 | Ha-ras | 20 nM | 70% | 30% |
| " | " | " | 50 nM | 51% | 49% |
| " | " | " | 100 nM | 44% | 56% |
| 17552 | 5 | control | 20 nM | 111% | — |
| " | " | " | 50 nM | 97% | 3% |
| " | " | " | 100 nM | 85% | 15% |

Induction of VCAM-1 by TNF-α was also blocked by c-raf (ISIS 12854, SEQ ID NO. 2) and Ha-ras (ISIS 15168, SEQ ID NO. 4) antisense oligonucleotides. Maximum inhibition for ISIS 12854 (SEQ ID NO. 2) was greater than 70%, while maximum inhibition for ISIS 15168 (SEQ ID NO. 4) was greater than 50%.

Example 6: Effect of c-raf and Ha-ras Antisense Oligonucleotides on Cell Adhesion Molecule mRNA levels Northern blot analysis was carried out to examine whether c-raf and Ha-ras antisense oligonucleotides inhibit the induction of cell adhesion molecules at the transcriptional level. Cells were treated with c-raf (ISIS 12854, SEQ ID NO. 2) or Ha-ras (ISIS 15168, SEQ ID NO. 4) antisense oligonucleotides and allowed to recover for 48 hrs. TNF-α was added two to three hours prior to RNA analysis and Northern blotting was performed with probes specific for E-selectin, ICAM-1, and VCAM-1. The probe for E-selectin was obtained by PCR amplification using primers directed to HUMELAM1A (Genbank Accession No. M24736; SEQ ID NO. 18).

The probe for ELAM-1 was obtained by PCR amplification using the following primers:
FORWARD 5'-TTGAAGTCATGATTGCTTCACAGTT-3' SEQ ID NO. 20
REVERSE 5'-TTCTGATTCTTTTGAACTTAAAGGAT-3' SEQ ID NO. 21

The probe for ICAM-1 was obtained by PCR amplification using the following primers:
FORWARD 5'-CGCGGATCCGCGTACTCAGAGTT-3' SEQ ID NO. 22
REVERSE 5'-CGGAATTCCGTTCAGGGAGGCGT-3' SEQ ID NO. 23

The probe for VCAM-1 was obtained by PCR amplification using the following primers:
FORWARD 5'-CTTAAAATGCCTGGGAAGATGGTCGT-3' SEQ ID NO. 24
REVERSE 5'-ATCAAGCATTAGCTACACTTTTGATT-3' SEQ ID NO. 25

Results are shown in Table 8.

TABLE 8

Effect of c-raf and Ha-ras antisense oligonucleotides on induction of E-selectin, VCAM-1, and ICAM-1

| ISIS # | SEQ ID NO: | ASO Gene Target | Cell adhesion molecule | % mRNA Expression | % mRNA Inhibition |
|---|---|---|---|---|---|
| LIPOFECTIN ™ | — | — | — | 100% | — |
| 12854 | 2 | c-raf | E-selectin | 22% | 78% |
| " | " | " | ICAM-1 | 78% | 22% |
| " | " | " | VCAM-1 | 35% | 65% |
| 15727 | 3 | control | E-selectin | 103% | — |
| " | " | " | ICAM-1 | 107% | — |
| " | " | " | VCAM-1 | 113% | — |
| 15168 | 4 | Ha-ras | E-selectin | 13% | 87% |
| " | " | " | ICAM-1 | 73% | 27% |
| " | " | " | VCAM-1 | 29% | 71% |
| 17552 | 5 | control | E-selectin | 92% | 8% |
| " | " | " | ICAM-1 | 101% | — |
| " | " | " | VCAM-1 | 111% | — |

Induction of mRNA expression of the three cell adhesion molecules was attenuated by both antisense oligonucleotides, whereas treatment with control oligonucleotides exhibited little to no effect. The level of inhibition for each cell adhesion molecule at the mRNA level was consistent with the effects of c-raf and Ha-ras antisense treatment on the cell surface expression of cell adhesion molecules.

Example 7: Effect of c-raf Antisense Oligonucleotides on MAP Kinase Activities

To examine the effect of the c-raf antisense oligonucleotide (ISIS 12854, SEQ ID NO. 2) on ERK, JNK, and p38 MAPK activities stimulated by TNF-α, in vitro kinase assays were performed on extracts derived from cells treated with ISIS 12854 (SEQ ID NO. 2). Cells were treated with oligonucleotides and induced with cytokines. At the indicated time, cells were lysed on ice and debris was removed by centrifugation. Protein concentration was measured by Bradford assay. Lysate containing equal amounts of protein were incubated with primary antibody-agarose conjugates (ERK and p38 assay; Santa Cruz Biotechnology, Santa Cruz, Calif.), or with JNK1-specific or JNK2-specific antibodies (JNK assay; Upstate Biotechnology, Lake Placid, N.Y.), overnight at 4° C.

For isoform-specific JNK assays, anti-rabbit IgG conjugated with agarose beads was added to cell extracts following JNK antibody treatment and wash steps and incubated for 2 hours at 4° C. After washing with lysis buffer and kinase buffer, the pelleted beads were incubated with 1 µg of substrate (Elk-1 for ERK, ATF-2 for p38, and c-Jun for JNK MAPK) and 100 αM of ATP for 20 minutes at 37° C. MAPK and JNK assay kits, ATF-2 fusion protein, and antibodies for ATF-2, Elk-1 phospho-ATF-2 were purchased from New England BioLabs (Boston, Mass.). Reactions were terminated by the addition of 3×SDS sample buffer followed by boiling. The samples were loaded on 12% SDS-PAGE gels. Western blot with antibodies specific for phosphorylated substrates (New England Biolabs) was carried out. The results were visualized by ECL.

Figure 3:
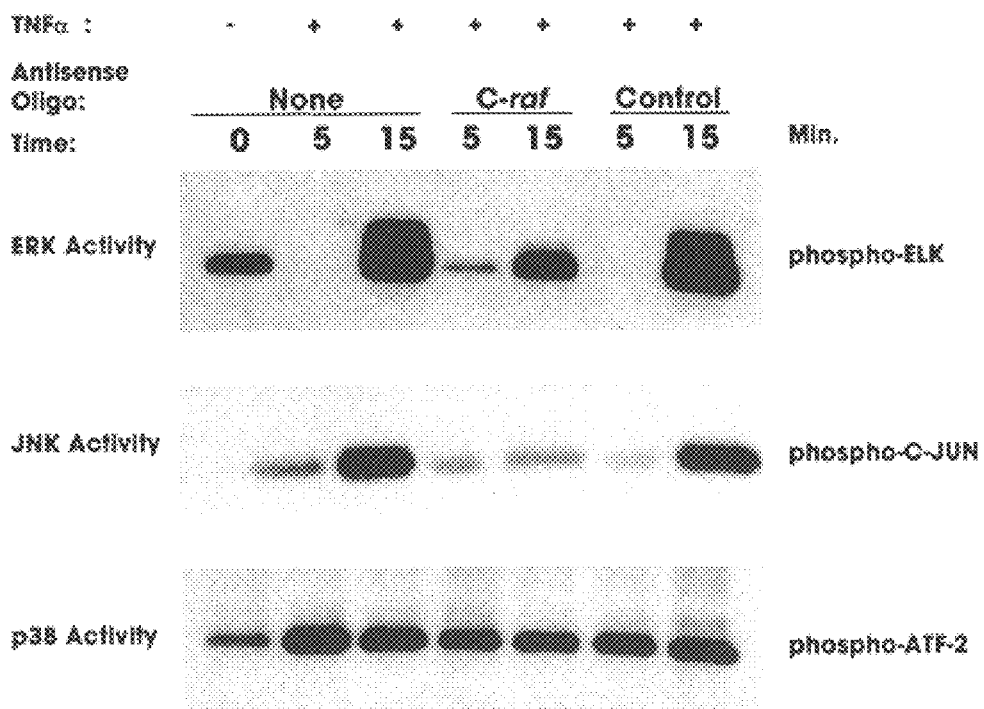
FIG. 3 is a Western blot showing the effects of c-raf antisense oligonucleotides on TNF-α mediated ERK, JNK and p38 kinase activities. Phospho-substrate-specific antibodies were used to analyze kinase activities.

Cells were treated with the c-raf antisense compound, ISIS 12854 (SEQ ID NO. 2), allowed to recover for 48 hours, at which time TNF-α was added for 5 or 15 minutes prior to cell lysis and initiation of the kinase assays. Specific antibody-conjugated agarose beads were used to immunoprecipitate ERK and p38 MAPK, and c-Jun-conjugated agarose beads were used to precipitate JNK. Suitable substrates and ATP were added to the immunoprecipitated kinase complexes and the reaction mixes were analyzed on SDS-PAGE. Western blotting with antibodies specific for phosphorylated substrates was carried out to determine relative kinase activity. Results are shown in FIG. 3.

All three kinases were activated by TNF-α after a 15 minutes incubation, as indicated by the heavy phosphorylation of the three substrates. Inhibition of c-raf levels by ISIS 12854 (SEQ ID NO. 2) resulted in reduced ERK activity. Surprisingly, JNK activity was also inhibited by treating cells with ISIS 12854 (SEQ ID NO. 2). Activation of p38 MAPK was not affected by c-raf antisense treatment.

Figure 4:
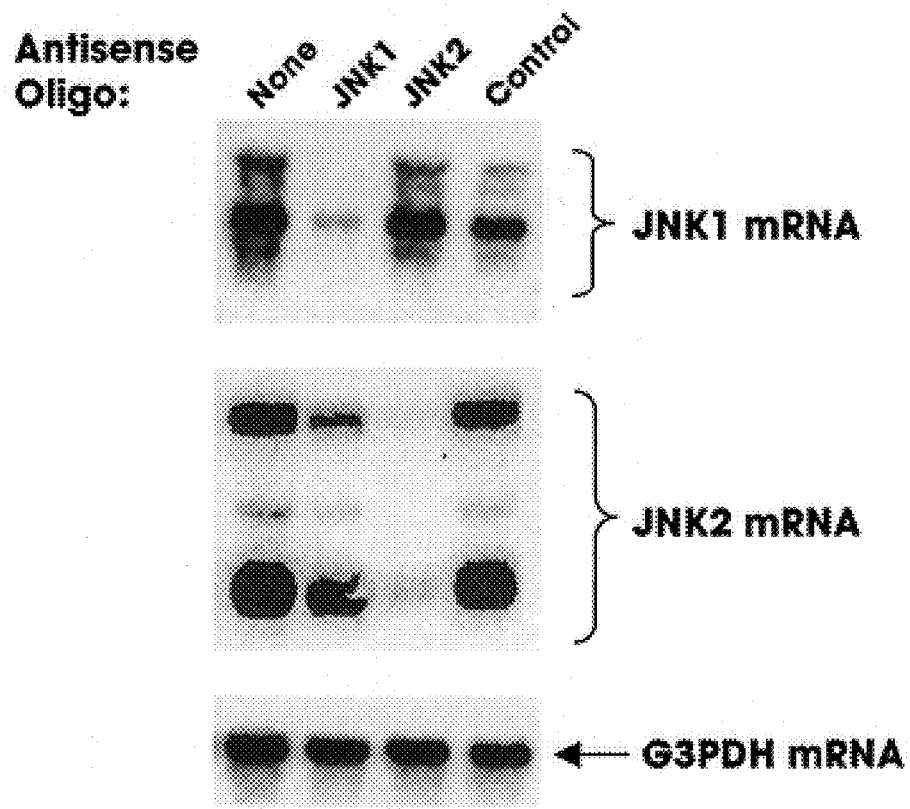
FIG. 4 is Northern blot showing the effects of JNK1 and JNK2 antisense oligonucleotides on TNF-α mediated JNK1 and JNK2 mRNA expression.
Figure 5:
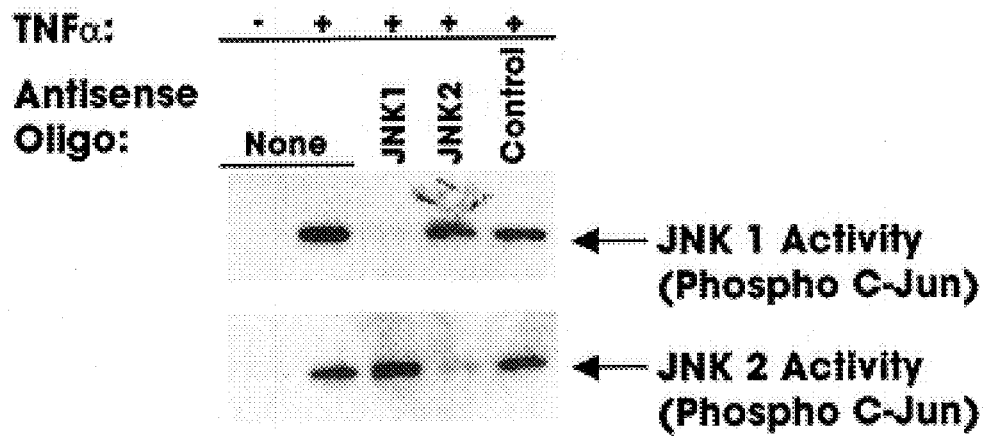
FIG. 5 is a Western blot showing the effects of JNK1 and JNK2 antisense oligonucleotides on TNF-α mediated JNK1 and JNK2 kinase activity. Phospho-substrate-specific antibodies were used to analyze kinase activities.

These results demonstrate for the first time that c-raf inhibition blocks TNF-α-mediated induction of cell adhesion molecules by suppressing the JNK pathway. Antisense oligonucleotides targeted against JNK1 (SEQ ID NO. 6) or JNK2 (SEQ ID NO. 7) were tested for their abilities to inhibit JNK expression, JNK activity and E-selectin induction by TNF-α. Oligonucleotide treatment, RNA isolation and Northern blots were performed as described in Example 2. A cDNA clone of JNK1 (Derijard et al., *Cell*, 1994, 76, 1025) was radiolabeled and used as a JNK1-specific probe. A cDNA clone of JNK2 (Kallunki et al., *Genes & Development*, 1994, 8, 2996) was radiolabeled and used as a JNK2-specific probe. JNK1 and JNK2 antisense treatment resulted in nearly complete inhibition of JNK1 and JNK2 mRNA expression, respectively, as shown in FIG. 4. Furthermore, both antisense oligonucleotides were isoform-specific at the employed concentrations. The JNK2 antisense molecule will inhibit JNK1 expression slightly at higher oligonucleotide concentrations due to the fact that it is complementary to JNK1 mRNA in 17 of its 20 bases. However, at the concentration tested, the JNK2 antisense oligonucleotide specifically inhibits JNK2 expression without affecting JNK1 levels. Treatment of cells with either JNK1 or JNK2 antisense effectively reduced TNF-α-mediated induction of JNK activity in an isoform-specific manner, as shown in FIG. 5. However, JNK2 antisense treatment resulted in substantially greater inhibition of TNF-α-mediated induction of E-selectin cell surface expression relative to JNK1 antisense treatment. Results are shown in Table 9. These results further confirm that the involvement of c-raf in TNF-α-mediated induction of cell adhesion molecules in HMVEC involves the regulation of JNK and that this regulation is believed to be specific for the JNK2 isoform.

TABLE 9

Dose Response of the Effect of JNK Antisense oligonucleotides in induction of E-selectin

| ISIS # | SEQ ID NO: | ASO Gene Target | Time (hours) | % Cell Surface Expression | % Cell Surface Inhibition |
|---|---|---|---|---|---|
| LIPOFECTIN | — | — | — | 100% | — |
| 15347 | 6 | JNK1 | 20 nM | 89% | 11% |
| " | " | " | 50 nM | 84% | 16% |
| " | " | " | 100 nM | 82% | 18% |
| 15354 | 7 | JNK2 | 20 nM | 32% | 68% |
| " | " | " | 50 nM | 29% | 71% |
| " | " | " | 100 nM | 33% | 67% |
| 15727 | 3 | control | 20 nM | 137% | — |
| " | " | " | 50 nM | 128% | — |
| " | " | " | 100 nM | 124% | — |

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: antisense sequence

<400> SEQUENCE: 1
gaagtcagcc aagaacagct                    20

<210> SEQ ID NO 2
<211> LENGTH: 20
<212> TYPE: DNA
<213> ORGANISM: Artificial Sequence

```
<220> FEATURE:
<223> OTHER INFORMATION: antisense sequence

<400> SEQUENCE: 2
tcccgcctgt gacatgcatt                                                     20

<210> SEQ ID NO 3
<211> LENGTH: 20
<212> TYPE: DNA
<213> ORGANISM: Artificial Sequence
<220> FEATURE:
<223> OTHER INFORMATION: control sequence

<400> SEQUENCE: 3
atgcattctg cccccaagga                                                     20

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
tccgtcatcg ctcctcaggg                                                     20

<210> SEQ ID NO 5
<211> LENGTH: 20
<212> TYPE: DNA
<213> ORGANISM: Artificial Sequence
<220> FEATURE:
<223> OTHER INFORMATION: control sequence

<400> SEQUENCE: 5
tcagtaatag ccccacatgg                                                     20

<210> SEQ ID NO 6
<211> LENGTH: 20
<212> TYPE: DNA
<213> ORGANISM: Artificial Sequence
<220> FEATURE:
<223> OTHER INFORMATION: antisense sequence

<400> SEQUENCE: 6
ctctctgtag gcccgcttgg                                                     20

<210> SEQ ID NO 7
<211> LENGTH: 20
<212> TYPE: DNA
<213> ORGANISM: Artificial Sequence
<220> FEATURE:
<223> OTHER INFORMATION: antisense sequence

<400> SEQUENCE: 7
gtccgggcca ggccaaagtc                                                     20

<210> SEQ ID NO 8
<211> LENGTH: 1072
<212> TYPE: DNA
<213> ORGANISM: Homo sapiens
<220> FEATURE:
<221> NAME/KEY: CDS
<222> LOCATION: (882)..(917)
<300> PUBLICATION INFORMATION:
<308> DATABASE ACCESSION NUMBER: M61895/Genbank
<309> DATABASE ENTRY DATE: 1994-11-07
```

-continued

<400> SEQUENCE: 8

| atccacagct | atgaatgaga | aattgaaggt | agtagactat | ggatgacaaa | cctattcttg | 60 |
| gtttccttct | gtttctgaaa | ttctaattac | taccacaact | acatgagaga | cactactaac | 120 |
| aagcaaagtt | ttacaactttt | ttaaagacat | agactttatg | ttattataat | taaaaatcat | 180 |
| gcatttttgt | catattaata | aaattgcata | tacgatataa | aggcatggac | aaaggtgaag | 240 |
| tagcttcaag | agacagagtt | tctgacatca | ttgtaatttt | aagcatcgtg | gatattccg | 300 |
| ggaaagtttt | tggatgccat | tgggatttc | ctctttactg | gatgtggaca | atatcctcct | 360 |
| attattcaca | ggaagcaatc | cctcctataa | aagggcctca | gccgaagtag | tgttcagctg | 420 |
| ttcttggctg | acttcacatc | aaaactccta | tactgacctg | agacagaggc | agcagtgata | 480 |
| cccacctgag | agatcctgtg | tttgaacaac | tgcttcccaa | aacggtaagt | gcagaacgct | 540 |
| ttataagggc | agcctcgggc | catgaaacac | agatatgcaa | aaggccttct | aataaaaacc | 600 |
| acatctgtac | aagctcttat | tgtattgtag | ctaaaacctg | tcttttctct | ttgacctaaa | 660 |
| taatgaaagt | cttaaaattt | gtttatttat | ttgattaaac | tctgaaataa | agattattgc | 720 |
| actagtgtcc | tttgcccaaa | atcttaggat | gctgccttaa | acatcatggt | agaataatgt | 780 |
| aactagctac | ccacgatttc | cttctttaat | tcatttgtgt | tttatctccc | caggaaagta | 840 |
| tttcaagcct | aaacctttgg | gtgaaaagaa | ctcttgaagt | c atg att gct tca cag | 896 |
| | | | | Met Ile Ala Ser Gln | |
| | | | | 1 5 | |

| ttt ctc tca gct ctc act ttg ggtaagtcag tgccattaga ccaagatttc | 947 |
| Phe Leu Ser Ala Leu Thr Leu | |
| 10 | |

| tcattctcgc actatagata tttcagactg aaatatcctt gcttgtctgg ggctgtcctg | 1007 |
| cacaggatat ctggcagcat ccttgacctc tacctgcaat gtgttcttcc ctgggcttgg | 1067 |
| ggtca | 1072 |

<210> SEQ ID NO 9
<211> LENGTH: 12
<212> TYPE: PRT
<213> ORGANISM: Homo sapiens

<400> SEQUENCE: 9

Met Ile Ala Ser Gln Phe Leu Ser Ala Leu Thr Leu
1               5                   10

<210> SEQ ID NO 10
<211> LENGTH: 6453
<212> TYPE: DNA
<213> ORGANISM: Homo sapiens
<220> FEATURE:
<221> NAME/KEY: CDS
<222> LOCATION: (1664)..(1774)
<220> FEATURE:
<221> NAME/KEY: CDS
<222> LOCATION: (2042)..(2220)
<220> FEATURE:
<221> NAME/KEY: CDS
<222> LOCATION: (2374)..(2533)
<220> FEATURE:
<221> NAME/KEY: CDS
<222> LOCATION: (3231)..(3350)
<300> PUBLICATION INFORMATION:
<308> DATABASE ACCESSION NUMBER: V00574/Genbank
<309> DATABASE ENTRY DATE: 1991-01-03

<400> SEQUENCE: 10
ggatcccagc ctttccccag cccgtagccc cgggacctcc gcggtgggcg gcgccgcgct    60

```
gccggcgcag ggagggcctc tggtgcaccg gcaccgctga gtcgggttct ctcgccggcc      120
tgttcccggg agagcccggg gccctgctcg gagatgccgc cccgggcccc agacaccgg       180 ctccctggcc ttcctcgagc aacccgagc tcggctccgg tctccagcca agcccaaccc      240
cgagaggccg cggccctact ggctccgcct cccgcgttgc tcccggaagc cccgcccgac      300
cgcggctcct gacagacggg ccgctcagcc aaccggggtg gggcggggcc cgatggcgcg     360
cagccaatgg taggccgcgc ctggcagacg gacgggcgcg gggcggggcg tgcgcaggcc      420
cgcccgagtc tccgccgccc gtgccctgcg cccgcaaccc gagccgcacc cgccgcggac     480
ggagcccatg cgcggggcga accgcgcgcc cccgcccccg ccccgccccg gcctcggccc     540
cggccctggc cccgggggca gtcgcgcctg tgaacggtga gtgcgggcag ggatcggccg     600
ggccgcgcgc cctcctcgcc cccaggcggc agcaatacgc gcggcgcggg ccggggcgc      660 ggggccggcg ggcgtaagcg gcggcggcgg cggcgggtgg gtggggccgg gcggggcccg     720
cgggcacagg tgagcgggcg tcggggctg cggcgggcgg gggccccttc ctccctgggg      780
cctgcgggaa tccggggccc acccgtggcc tcgcgctggg cacggtcccc acgccggcgt     840
acccgggagc ctcgggcccg gcgccctcac acccggggc gtctgggagg aggcggccgc      900
ggccacggca cgcccgggca ccccgattc agcatcacag gtcgcggacc aggccggggg      960
cctcagcccc agtgcctttt ccctctccgg gtctcccgcg ccgcttctcg gccccttcct    1020
gtcgctcagt ccctgcttcc caggagctcc tctgtcttct ccagctttct gtggctgaaa    1080
gatgcccccg gttccccgcc gggggtgcgg ggcgctgccc gggtctgccc tcccctcggc    1140
ggcgcctagt acgcagtagg cgctcagcaa atacttgtcg gaggcaccag cgccgcgggg    1200
cctgcaggct ggcactagcc tgcccgggca cgccgtggcg cgctccgccg tggccagacc    1260
tgttctggag gacggtaacc tcagcccctcg ggcgcctccc tttagccttt ctgccgaccc   1320
agcagcttct aatttgggtg cgtggttgag agcgctcagc tgtcagccct gcctttgagg    1380
gctgggtccc ttttcccatc actgggtcat taagagcaag tgggggcgag gcgacagccc    1440
tcccgcacgc tgggttgcag ctgcacaggt aggcacgctg cagtccttgc tgcctggcgt    1500
tggggcccag ggaccgctgt gggtttgccc ttcagatggc cctgccagca gctgccctgt    1560
ggggcctggg gctgggcctg gcctggctg agcagggccc tccttggcag gtggggcagg    1620
agaccctgta ggaggacccc gggccgcagg cccctgagga gcg atg acg gaa tat     1675
                                             Met Thr Glu Tyr
                                               1 aag ctg gtg gtg gtg ggc gcc ggc ggt gtg ggc aag agt gcg ctg acc      1723
Lys Leu Val Val Val Gly Ala Gly Gly Val Gly Lys Ser Ala Leu Thr
  5              10                  15                  20 atc cag ctg atc cag aac cat ttt gtg gac gaa tac gac ccc act ata      1771
Ile Gln Leu Ile Gln Asn His Phe Val Asp Glu Tyr Asp Pro Thr Ile
          25                  30                  35 gag gtgagcctgg cgccaccgtc caggtgccag cagctgctgc gggcgagccc           1824
Glu aggacacagc caggataggg ctggctgcag cccctggtcc cctgcatggt gctgtggccc    1884
tgtctcctgc ttcctctaga ggaggggagt ccctcgtctc agcaccccag agaggaggg     1944 ggcatgaggg gcatgagagg taccaggag aggctggctg tgtgaactcc ccccacggaa    2004
ggtcctgagg gggtccctga gccctgtcct cctgcag gat tcc tac cgg aag cag    2059
                                        Asp Ser Tyr Arg Lys Gln
                                                          40 gtg gtc att gat ggg gag acg tgc ctg ttg gac atc ctg gat acc gcc      2107
Val Val Ile Asp Gly Glu Thr Cys Leu Leu Asp Ile Leu Asp Thr Ala
```

```
             45                  50                  55
ggc cag gag gag tac agc gcc atg cgg gac cag tac atg cgc acc ggg     2155
Gly Gln Glu Glu Tyr Ser Ala Met Arg Asp Gln Tyr Met Arg Thr Gly
 60                  65                  70                  75
gag ggc ttc ctg tgt gtg ttt gcc atc aac aac acc aag tct ttt gag     2203
Glu Gly Phe Leu Cys Val Phe Ala Ile Asn Asn Thr Lys Ser Phe Glu
                 80                  85                  90
gac atc cac cag tac agg tgaaccccgt gaggctggcc cgggagccca             2251
Asp Ile His Gln Tyr Arg
                 95 cgccgcacag gtggggccag gccggctgcg tccaggcagg ggcctcctgt cctctctgcg    2311 catgtcctgg atgccgctgc gcctgcagcc cccgtagcca gctctcgctt tccacctctc    2371 agg gag cag atc aaa cgg gtg aag gac tcg gat gac gtg ccc atg gtg     2419
    Glu Gln Ile Lys Arg Val Lys Asp Ser Asp Asp Val Pro Met Val
            100                 105                 110 ctg gtg ggg aac aag tgt gac ctg gct gca cgc act gtg gaa tct cgg     2467
Leu Val Gly Asn Lys Cys Asp Leu Ala Ala Arg Thr Val Glu Ser Arg
        115                 120                 125 cag gct cag gac ctc gcc cga agc tac ggc atc ccc tac atc gag acc     2515
Gln Ala Gln Asp Leu Ala Arg Ser Tyr Gly Ile Pro Tyr Ile Glu Thr
    130                 135                 140 tcg gcc aag acc cgg cag gtgaggcagc tctccacccc acagctagcc             2563
Ser Ala Lys Thr Arg Gln
145             150 agggacccgc cccgccccgc cccagccagg gagcagcact cactgaccct ctcccttgac    2623
acagggcagc cgctctggct ctagctccag ctccgggacc ctctgggacc cccgggacc     2683 catgtgaccc agcggcccct cgcgctgtaa gtctcccggg acgcagggc agtgagggag     2743 gcgagggccg gggtctgggc tcacgccctg cagtcctggg ccgacacagc tccggggaag    2803
gcggaggtcc ttggggagag ctgccctgag ccaggccgga gcggtgaccc tggggcccgg    2863
cccctcttgt ccccagagtg tcccacgggc acctgttggt tctgagtctt agtggggcta    2923
ctggggacac gggccgtagc tgagtcgaga gctgggtgca gggtggtcaa ccctggcca     2983 gacctggagt tcaggagggc cccgggccac cctgaccttt gagggctgc tgtagcatga    3043 tgcgggtggc cctgggcact tcgagatggc cagagtccag cttcccgtgt gtgtggtggg    3103
cctggggaag tggctggtgg agtcgggagc ttcgggccag gcaaggcttg atcccacagc    3163
agggagcccc tcacccaggc aggcggccac aggccggtcc ctcctgatcc catccctcct    3223 ttcccag gga gtg gag gat gcc ttc tac acg ttg gtg cgt gag atc cgg     3272
        Gly Val Glu Asp Ala Phe Tyr Thr Leu Val Arg Glu Ile Arg
                    155                 160
cag cac aag ctg cgg aag ctg aac cct cct gat gag agt ggc ccc ggc     3320
Gln His Lys Leu Arg Lys Leu Asn Pro Pro Asp Glu Ser Gly Pro Gly
165                 170                 175                 180 tgc atg agc tgc aag tgt gtg ctc tcc tga cgcaggtgag ggggactccc        3370
Cys Met Ser Cys Lys Cys Val Leu Ser
                185 agggcggccg ccacgcccac cggatgaccc cggctccccg cccctgccgg tctcctggcc    3430 tgcggtcagc agcctcccct tgtccccgcc cagcacaagc tcaggacatg gaggtgccgg    3490 atgcaggaag gaggtgcaga cggaaggagg aggaaggaag gacggaagca aggaaggaag    3550 gaagggctgc tggagcccag tcaccccggg accgtgggcc gaggtgactg cagaccctcc    3610 cagggaggct gtgcacagac tgtcttgaac atcccaaatg ccaccggaac cccagccctt    3670 agctcccctc ccaggcctct gtgggccctt gtcgggcaca gatgggatca cagtaaatta    3730 ttggatggtc ttgatcttgg ttttcggctg agggtgggac acgtgcgcg tgtggcctgg    3790 catgaggtat gtcggaacct caggcctgtc cagccctggg ctctccatag cctttgggag    3850
```

-continued

```
ggggaggttg ggagaggccg gtcaggggtc tgggctgtgg tgctctctcc tcccgcctgc    3910
cccagtgtcc acggcttctg gcagagagct ctggacaagc aggcagatca taaggacaga    3970
gagcttactg tgcttctacc aactaggagg gcgtcctggt cctccagagg gaggtggttt    4030
caggggttgg ggatctgtgc cggtggctct ggtctctgct gggagccttc ttggcggtga    4090
gaggcatcac ctttcctgac ttgctcccag cgtgaaatgc acctgccaag aatggcagac    4150
atagggaccc cgcctcctgg gccttacat gcccagtttt cttcggctct gtggcctgaa    4210
gcggtctgtg gaccttggaa gtagggctcc agcaccgact ggcctcaggc ctctgcctca    4270
ttggtggtcg ggtagcggcc agtagggcgt gggagcctgg ccatccctgc ctcctggagt    4330
ggacgaggtt ggcagctggt ccgtctgctc ctgccccact ctcccccgcc cctgccctca    4390
ccctacccct gccccacgcc tgcctcatgg ctggttgctc ttggagcctg gtagtgtcac    4450
tggctcagcc ttgctgggta tacacaggct ctgccaccca ctctgctcca aggggcttgc    4510
cctgccttgg gccaagttct aggtctggcc acagccacag acagctcagt cccctgtgtg    4570
gtcatcctgg cttctgctgg gggcccacag cgccctggt gcccctcccc tcccagggcc    4630
cgggttgagg ctgggccagg ccctctggga cggggacttg tgccctgtca gggttcccta    4690
tccctgaggt tgggggagag ctagcagggc atgccgctgg ctggccaggg ctgcagggac    4750
actccccctt ttgtccaggg aataccacac tcgcccttct ctccagcgaa caccacactc    4810
gcccttctct ccaggggacg ccacactccc ccttctgtcc aggggacgcc acactccccc    4870
ttctctccag gggacgccac actcgccctt ctctccaggg gacgccacac tcgcccttct    4930
ctccagggga cgccacactc gcccttctgt ccaggggacg ccacactcgc ccttctctcc    4990 agggggacgcc acactcgccc ttctctccag gggacgccac actcccccctt ctgtccaggg    5050 gacgccacac tcccccttct ctccaggggga cgccacactc cccccttctct ccaggggacg    5110 ccacactcgc ccttctctcc agggggacgcc acactccccc ttctgtccag gggacgccac    5170 actcgcccctt ctctccaggg gacgccacac tcgcccttct ctccaggggga cgccacactc    5230 ccccttctct ccaggggacg ccacactccc ccttctctcc agggggacgcc acactccccc    5290 ttctgtccag gggacgccac actcgcccctt ctctccaggg gacgccacac tccccccttct    5350 ctccagggga cgccacactc cccctttctct caggggacg ccacactccc ccttctgtcc    5410
aggggacgcc acactcgccc ttctctccag gggacgccac actcgcccctt ctctccaggg    5470 gacgccacac tcgcccttct ctccagggga cgccacactt gcccttctgt cagggaatg    5530 ccacactccc ccttctcccc agcagcctcc gagtgaccag cttccccatc gatagacttc    5590
ccgaggccag gagccctcta gggctgccgg gtgccaccct ggctccttcc acaccgtgct    5650
ggtcactgcc tgctggggggc gtcagatgca ggtgaccctg tgcaggaggt atctctggac    5710
ctgcctcttg gtcattacgg ggctgggcag ggcctggtat cagggccccg ctggggttgc    5770
agggctgggc ctgtgctgtg gtcctggggt gtccaggaca gacgtggagg ggtcagggcc    5830
cagcacccct gctccatgct gaactgtggg aagcatccag gtccctgggt ggcttcaaca    5890
ggagttccag cacgggaacc actggacaac ctgggtgtg tcctgatctg ggacaggcc    5950 agccacaccc cgagtcctag ggactccaga gagcagccca ctgccctggg ctccacggaa    6010 gcccctcat gccgctaggc cttggcctcg gggacagccc agctaggcca gtgtgtggca    6070
ggaccaggcc cccatgtggg agctgacccc ttgggattct ggagctgtgc tgatgggcag    6130
gggagagcca gctcctcccc ttgagggagg gtcttgatgc ctggggttac ccgcagaggc    6190
ctgggtgccg ggacgctccc cggtttggct gaaaggaaag cagatgtggt cagcttctcc    6250
```

-continued

```
actgagccca tctggtcttc ccggggctgg gccccataga tctgggtccc tgtgtggccc    6310
ccctggtctg atgccgagga taccoctgca aactgccaat cccagaggac aagactggga    6370
agtccctgca gggagagccc atccccgcac cctgacccac aagagggact cctgctgccc    6430
accaggcatc cctccaggga tcc                                            6453
```

<210> SEQ ID NO 11
<211> LENGTH: 189
<212> TYPE: PRT
<213> ORGANISM: Homo sapiens

<400> SEQUENCE: 11

```
Met Thr Glu Tyr Lys Leu Val Val Gly Ala Gly Gly Val Gly Lys
  1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gln Glu Glu Tyr
     50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 12
<211> LENGTH: 2977
<212> TYPE: DNA
<213> ORGANISM: Homo sapiens
<220> FEATURE:
<221> NAME/KEY: CDS
<222> LOCATION: (130)..(2076)
<300> PUBLICATION INFORMATION:
<308> DATABASE ACCESSION NUMBER: X03484/Genbank
<309> DATABASE ENTRY DATE: 1993-09-12

<400> SEQUENCE: 12

```
ccgaatgtga ccgcctcccg ctccctcacc cgccgcgggg aggaggagcg ggcgagaagc    60
tgccgccgaa cgacaggacg ttggggcggc ctggctccct caggtttaag aattgtttaa   120 gctgcatca atg gag cac ata cag gga gct tgg aag acg atc agc aat ggt    171
          Met Glu His Ile Gln Gly Ala Trp Lys Thr Ile Ser Asn Gly
            1               5                  10 ttt gga ttc aaa gat gcc gtg ttt gat ggc tcc agc tgc atc tct cct     219
Phe Gly Phe Lys Asp Ala Val Phe Asp Gly Ser Ser Cys Ile Ser Pro
 15                  20                  25                  30
```

```
aca ata gtt cag cag ttt ggc tat cag cgc cgg gca tca gat gat ggc    267
Thr Ile Val Gln Gln Phe Gly Tyr Gln Arg Arg Ala Ser Asp Asp Gly
             35                  40                  45 aaa ctc aca gat cct tct aag aca agc aac act atc cgt gtt ttc ttg    315
Lys Leu Thr Asp Pro Ser Lys Thr Ser Asn Thr Ile Arg Val Phe Leu
         50                  55                  60 ccg aac aag caa aga aca gtg gtc aat gtg cga aat gga atg agc ttg    363
Pro Asn Lys Gln Arg Thr Val Val Asn Val Arg Asn Gly Met Ser Leu
         65                  70                  75 cat gac tgc ctt atg aaa gca ctc aag gtg agg ggc ctg caa cca gag    411
His Asp Cys Leu Met Lys Ala Leu Lys Val Arg Gly Leu Gln Pro Glu
     80                  85                  90 tgc tgt gca gtg ttc aga ctt ctc cac gaa cac aaa ggt aaa aaa gca    459
Cys Cys Ala Val Phe Arg Leu Leu His Glu His Lys Gly Lys Lys Ala
 95                 100                 105                 110 cgc tta gat tgg aat act gat gct gcg tct ttg att gga gaa gaa ctt    507
Arg Leu Asp Trp Asn Thr Asp Ala Ala Ser Leu Ile Gly Glu Glu Leu
                115                 120                 125 caa gta gat ttc ctg gat cat gtt ccc ctc aca aca cac aac ttt gct    555
Gln Val Asp Phe Leu Asp His Val Pro Leu Thr Thr His Asn Phe Ala
            130                 135                 140 cgg aag acg ttc ctg aag ctt gcc ttc tgt gac atc tgt cag aaa ttc    603
Arg Lys Thr Phe Leu Lys Leu Ala Phe Cys Asp Ile Cys Gln Lys Phe
        145                 150                 155 ctg ctc aat gga ttt cga tgt cag act tgt ggc tac aaa ttt cat gag    651
Leu Leu Asn Gly Phe Arg Cys Gln Thr Cys Gly Tyr Lys Phe His Glu
    160                 165                 170 cac tgt agc acc aaa gta cct act atg tgt gtg gac tgg agt aac atc    699
His Cys Ser Thr Lys Val Pro Thr Met Cys Val Asp Trp Ser Asn Ile
175                 180                 185                 190 aga caa ctc tta ttg ttt cca aat tcc act att ggt gat agt gga gtc    747
Arg Gln Leu Leu Leu Phe Pro Asn Ser Thr Ile Gly Asp Ser Gly Val
                195                 200                 205 cca gca cta cct tct ttg act atg cgt cgt atg cga gag tct gtt tcc    795
Pro Ala Leu Pro Ser Leu Thr Met Arg Arg Met Arg Glu Ser Val Ser
            210                 215                 220 agg atg cct gtt agt tct cag cac aga tat tct aca cct cac gcc ttc    843
Arg Met Pro Val Ser Ser Gln His Arg Tyr Ser Thr Pro His Ala Phe
        225                 230                 235 acc ttt aac acc tcc agt ccc tca tct gaa ggt tcc ctc tcc cag agg    891
Thr Phe Asn Thr Ser Ser Pro Ser Ser Glu Gly Ser Leu Ser Gln Arg
    240                 245                 250 cag agg tcg aca tcc aca cct aat gtc cac atg gtc agc acc acg ctg    939
Gln Arg Ser Thr Ser Thr Pro Asn Val His Met Val Ser Thr Thr Leu
255                 260                 265                 270 cct gtg gac agc agg atg att gag gat gca att cga agt cac agc gaa    987
Pro Val Asp Ser Arg Met Ile Glu Asp Ala Ile Arg Ser His Ser Glu
                275                 280                 285 tca gcc tca cct tca gcc ctg tcc agt agc ccc aac aat ctg agc cca   1035
Ser Ala Ser Pro Ser Ala Leu Ser Ser Ser Pro Asn Asn Leu Ser Pro
            290                 295                 300 aca ggc tgg tca cag ccg aaa acc ccc gtg cca gca caa aga gag cgg   1083
Thr Gly Trp Ser Gln Pro Lys Thr Pro Val Pro Ala Gln Arg Glu Arg
        305                 310                 315 gca cca gta tct ggg acc cag gag aaa aac aaa att agg cct cgt gga   1131
Ala Pro Val Ser Gly Thr Gln Glu Lys Asn Lys Ile Arg Pro Arg Gly
    320                 325                 330 cag aga gat tca agc tat tat tgg gaa ata gaa gcc agt gaa gtg atg   1179
Gln Arg Asp Ser Ser Tyr Tyr Trp Glu Ile Glu Ala Ser Glu Val Met
335                 340                 345                 350
```

```
ctg tcc act cgg att ggg tca ggc tct ttt gga act gtt tat aag ggt      1227
Leu Ser Thr Arg Ile Gly Ser Gly Ser Phe Gly Thr Val Tyr Lys Gly
                355                 360                 365 aaa tgg cac gga gat gtt gca gta aag atc cta aag gtt gtc gac cca      1275
Lys Trp His Gly Asp Val Ala Val Lys Ile Leu Lys Val Val Asp Pro
        370                 375                 380 acc cca gag caa ttc cag gcc ttc agg aat gag gtg gct gtt ctg cgc      1323
Thr Pro Glu Gln Phe Gln Ala Phe Arg Asn Glu Val Ala Val Leu Arg
    385                 390                 395 aaa aca cgg cat gtg aac att ctg ctt ttc atg ggg tac atg aca aag      1371
Lys Thr Arg His Val Asn Ile Leu Leu Phe Met Gly Tyr Met Thr Lys
400                 405                 410 gac aac ctg gca att gtg acc cag tgg tgc gag ggc agc agc ctc tac      1419
Asp Asn Leu Ala Ile Val Thr Gln Trp Cys Glu Gly Ser Ser Leu Tyr
415                 420                 425                 430 aaa cac ctg cat gtc cag gag acc aag ttt cag atg ttc cag cta att      1467
Lys His Leu His Val Gln Glu Thr Lys Phe Gln Met Phe Gln Leu Ile
                435                 440                 445 gac att gcc cgg cag acg gct cag gga atg gac tat ttg cat gca aag      1515
Asp Ile Ala Arg Gln Thr Ala Gln Gly Met Asp Tyr Leu His Ala Lys
            450                 455                 460 aac atc atc cat aga gac atg aaa tcc aac aat ata ttt ctc cat gaa      1563
Asn Ile Ile His Arg Asp Met Lys Ser Asn Asn Ile Phe Leu His Glu
        465                 470                 475 ggc tta aca gtg aaa att gga gat ttt ggt ttg gca aca gta aag tca      1611
Gly Leu Thr Val Lys Ile Gly Asp Phe Gly Leu Ala Thr Val Lys Ser
    480                 485                 490 cgc tgg agt ggt tct cag cag gtt gaa caa cct act ggc tct gtc ctc      1659
Arg Trp Ser Gly Ser Gln Gln Val Glu Gln Pro Thr Gly Ser Val Leu
495                 500                 505                 510 tgg atg gcc cca gag gtg atc cga atg cag gat aac aac cca ttc agt      1707
Trp Met Ala Pro Glu Val Ile Arg Met Gln Asp Asn Asn Pro Phe Ser
                515                 520                 525 ttc cag tcg gat gtc tac tcc tat ggc atc gta ttg tat gaa ctg atg      1755
Phe Gln Ser Asp Val Tyr Ser Tyr Gly Ile Val Leu Tyr Glu Leu Met
            530                 535                 540 acg ggg gag ctt cct tat tct cac atc aac aac cga gat cag atc atc      1803
Thr Gly Glu Leu Pro Tyr Ser His Ile Asn Asn Arg Asp Gln Ile Ile
        545                 550                 555 ttc atg gtg ggc cga gga tat gcc tcc cca gat ctt agt aag cta tat      1851
Phe Met Val Gly Arg Gly Tyr Ala Ser Pro Asp Leu Ser Lys Leu Tyr
    560                 565                 570 aag aac tgc ccc aaa gca atg aag agg ctg gta gct gac tgt gtg aag      1899
Lys Asn Cys Pro Lys Ala Met Lys Arg Leu Val Ala Asp Cys Val Lys
575                 580                 585                 590 aaa gta aag gaa gag agg cct ctt ttt ccc cag atc ctg tct tcc att      1947
Lys Val Lys Glu Glu Arg Pro Leu Phe Pro Gln Ile Leu Ser Ser Ile
                595                 600                 605 gag ctg ctc caa cac tct cta ccg aag atc aac cgg agc gct tcc gag      1995
Glu Leu Leu Gln His Ser Leu Pro Lys Ile Asn Arg Ser Ala Ser Glu
            610                 615                 620 cca tcc ttg cat cgg gca gcc cac act gag gat atc aat gct tgc acg      2043
Pro Ser Leu His Arg Ala Ala His Thr Glu Asp Ile Asn Ala Cys Thr
        625                 630                 635 ctg acc acg tcc ccg agg ctg cct gtc ttc tag ttgactttgc acctgtcttc   2096
Leu Thr Thr Ser Pro Arg Leu Pro Val Phe
    640                 645 aggctgccag gggaggagga gaagccagca ggcaccactt ttctgctccc tttctccaga    2156
```

-continued

```
ggcagaacac atgttttcag agaagctctg ctaaggacct tctagactgc tcacagggcc    2216
ttaacttcat gttgccttct tttctatccc tttgggccct gggagaagga agccatttgc    2276
agtgctggtg tgtcctgctc cctccccaca ttccccatgc tcaaggccca gccttctgta    2336
gatgcgcaag tggatgttga tggtagtaca aaaagcaggg gcccagcccc agctgttggc    2396
tacatgagta tttagaggaa gtaaggtagc aggcagtcca gccctgatgt ggagacacat    2456
gggattttgg aaatcagctt ctggaggaat gcatgtcaca ggcgggactt tcttcagaga    2516
gtggtgcagc gccagacatt tgcacataa ggcaccaaac agcccaggac tgccgagact     2576
ctggccgccc gaaggagcct gctttggtac tatggaactt ttcttagggg acacgtcctc    2636
ctttcacagc ttctaaggtg tccagtgcat tgggatggtt ttccaggcaa ggcactcggc    2696
caatccgcat ctcagccctc tcaggagcag tcttccatca tgctgaattt tgtcttccag    2756
gagctgcccc tatggggcgg gccgcagggc cagcctgttt ctctaacaaa caaacaaaca    2816
aacagccttg tttctctagt cacatcatgt gtatacaagg aagccaggaa tacaggtttt    2876
cttgatgatt tgggttttaa ttttgttttt attgcacctg acaaaataca gttatctgat    2936
ggtccctcaa ttatgttatt ttaataaaat aaattaaatt t                        2977
```

<210> SEQ ID NO 13
<211> LENGTH: 648
<212> TYPE: PRT
<213> ORGANISM: Homo sapiens

<400> SEQUENCE: 13

```
Met Glu His Ile Gln Gly Ala Trp Lys Thr Ile Ser Asn Gly Phe Gly
  1               5                  10                  15

Phe Lys Asp Ala Val Phe Asp Gly Ser Ser Cys Ile Ser Pro Thr Ile
                 20                  25                  30

Val Gln Gln Phe Gly Tyr Gln Arg Arg Ala Ser Asp Asp Gly Lys Leu
             35                  40                  45

Thr Asp Pro Ser Lys Thr Ser Asn Thr Ile Arg Val Phe Leu Pro Asn
         50                  55                  60

Lys Gln Arg Thr Val Val Asn Val Arg Asn Gly Met Ser Leu His Asp
     65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
        130                 135                 140

Thr Phe Leu Lys Leu Ala Phe Cys Asp Ile Cys Gln Lys Phe Leu Leu
    145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
    210                 215                 220

Pro Val Ser Ser Gln His Arg Tyr Ser Thr Pro His Ala Phe Thr Phe
```

```
                225               230               235               240
     Asn Thr Ser Ser Pro Ser Ser Glu Gly Ser Leu Ser Gln Arg Gln Arg
                     245               250               255
     Ser Thr Ser Thr Pro Asn Val His Met Val Ser Thr Thr Leu Pro Val
                 260               265               270
     Asp Ser Arg Met Ile Glu Asp Ala Ile Arg Ser His Ser Glu Ser Ala
             275               280               285
     Ser Pro Ser Ala Leu Ser Ser Pro Asn Asn Leu Ser Pro Thr Gly
         290               295               300
     Trp Ser Gln Pro Lys Thr Pro Val Pro Ala Gln Arg Glu Arg Ala Pro
     305               310               315               320
     Val Ser Gly Thr Gln Glu Lys Asn Lys Ile Arg Pro Arg Gly Gln Arg
                     325               330               335
     Asp Ser Ser Tyr Tyr Trp Glu Ile Glu Ala Ser Glu Val Met Leu Ser
                 340               345               350
     Thr Arg Ile Gly Ser Gly Ser Phe Gly Thr Val Tyr Lys Gly Lys Trp
             355               360               365
     His Gly Asp Val Ala Val Lys Ile Leu Lys Val Val Asp Pro Thr Pro
         370               375               380
     Glu Gln Phe Gln Ala Phe Arg Asn Glu Val Ala Val Leu Arg Lys Thr
     385               390               395               400
     Arg His Val Asn Ile Leu Leu Phe Met Gly Tyr Met Thr Lys Asp Asn
                     405               410               415
     Leu Ala Ile Val Thr Gln Trp Cys Glu Gly Ser Ser Leu Tyr Lys His
                 420               425               430
     Leu His Val Gln Glu Thr Lys Phe Gln Met Phe Gln Leu Ile Asp Ile
             435               440               445
     Ala Arg Gln Thr Ala Gln Gly Met Asp Tyr Leu His Ala Lys Asn Ile
         450               455               460
     Ile His Arg Asp Met Lys Ser Asn Asn Ile Phe Leu His Glu Gly Leu
     465               470               475               480
     Thr Val Lys Ile Gly Asp Phe Gly Leu Ala Thr Val Lys Ser Arg Trp
                     485               490               495
     Ser Gly Ser Gln Gln Val Glu Gln Pro Thr Gly Ser Val Leu Trp Met
                 500               505               510
     Ala Pro Glu Val Ile Arg Met Gln Asp Asn Asn Pro Phe Ser Phe Gln
             515               520               525
     Ser Asp Val Tyr Ser Tyr Gly Ile Val Leu Tyr Glu Leu Met Thr Gly
         530               535               540
     Glu Leu Pro Tyr Ser His Ile Asn Asn Arg Asp Gln Ile Ile Phe Met
     545               550               555               560
     Val Gly Arg Gly Tyr Ala Ser Pro Asp Leu Ser Lys Leu Tyr Lys Asn
                     565               570               575
     Cys Pro Lys Ala Met Lys Arg Leu Val Ala Asp Cys Val Lys Lys Val
                 580               585               590
     Lys Glu Glu Arg Pro Leu Phe Pro Gln Ile Leu Ser Ser Ile Glu Leu
             595               600               605
     Leu Gln His Ser Leu Pro Lys Ile Asn Arg Ser Ala Ser Glu Pro Ser
         610               615               620
     Leu His Arg Ala Ala His Thr Glu Asp Ile Asn Ala Cys Thr Leu Thr
     625               630               635               640
     Thr Ser Pro Arg Leu Pro Val Phe
                     645
```

<210> SEQ ID NO 14
<211> LENGTH: 1418
<212> TYPE: DNA
<213> ORGANISM: Homo sapiens
<220> FEATURE:
<221> NAME/KEY: CDS
<222> LOCATION: (19)..(1173)
<300> PUBLICATION INFORMATION:
<308> DATABASE ACCESSION NUMBER: L26318/Genbank
<309> DATABASE ENTRY DATE: 1994-04-25

<400> SEQUENCE: 14

| | | | | | | | | | | | | |
|---|---|---|---|---|---|---|---|---|---|---|---|---|
| cattaattgc ttgccatc | atg | agc | aga | agc | aag | cgt | gac | aac | aat | ttt | tat | 51 |
| | Met | Ser | Arg | Ser | Lys | Arg | Asp | Asn | Asn | Phe | Tyr | |
| | 1 | | | 5 | | | | | 10 | | | |
| agt gta gag att gga gat tct aca ttc aca gtc ctg aaa cga tat cag | | | | | | | | | | | | 99 |
| Ser Val Glu Ile Gly Asp Ser Thr Phe Thr Val Leu Lys Arg Tyr Gln | | | | | | | | | | | | |
| 15 20 25 | | | | | | | | | | | | |
| aat tta aaa cct ata ggc tca gga gct caa gga ata gta tgc gca gct | | | | | | | | | | | | 147 |
| Asn Leu Lys Pro Ile Gly Ser Gly Ala Gln Gly Ile Val Cys Ala Ala | | | | | | | | | | | | |
| 30 35 40 | | | | | | | | | | | | |
| tat gat gcc att ctt gaa aga aat gtt gca atc aag aag cta agc cga | | | | | | | | | | | | 195 |
| Tyr Asp Ala Ile Leu Glu Arg Asn Val Ala Ile Lys Lys Leu Ser Arg | | | | | | | | | | | | |
| 45 50 55 | | | | | | | | | | | | |
| cca ttt cag aat cag act cat gcc aag cgg gcc tac aga gag cta gtt | | | | | | | | | | | | 243 |
| Pro Phe Gln Asn Gln Thr His Ala Lys Arg Ala Tyr Arg Glu Leu Val | | | | | | | | | | | | |
| 60 65 70 75 | | | | | | | | | | | | |
| ctt atg aaa tgt gtt aat cac aaa aat ata att ggc ctt ttg aat gtt | | | | | | | | | | | | 291 |
| Leu Met Lys Cys Val Asn His Lys Asn Ile Ile Gly Leu Leu Asn Val | | | | | | | | | | | | |
| 80 85 90 | | | | | | | | | | | | |
| ttc aca cca cag aaa tcc cta gaa gaa ttt caa gat gtt tac ata gtc | | | | | | | | | | | | 339 |
| Phe Thr Pro Gln Lys Ser Leu Glu Glu Phe Gln Asp Val Tyr Ile Val | | | | | | | | | | | | |
| 95 100 105 | | | | | | | | | | | | |
| atg gag ctc atg gat gca aat ctt tgc caa gtg att cag atg gag cta | | | | | | | | | | | | 387 |
| Met Glu Leu Met Asp Ala Asn Leu Cys Gln Val Ile Gln Met Glu Leu | | | | | | | | | | | | |
| 110 115 120 | | | | | | | | | | | | |
| gat cat gaa aga atg tcc tac ctt ctc tat cag atg ctg tgt gga atc | | | | | | | | | | | | 435 |
| Asp His Glu Arg Met Ser Tyr Leu Leu Tyr Gln Met Leu Cys Gly Ile | | | | | | | | | | | | |
| 125 130 135 | | | | | | | | | | | | |
| aag cac ctt cat tct gct gga att att cat cgg gac tta aag ccc agt | | | | | | | | | | | | 483 |
| Lys His Leu His Ser Ala Gly Ile Ile His Arg Asp Leu Lys Pro Ser | | | | | | | | | | | | |
| 140 145 150 155 | | | | | | | | | | | | |
| aat ata gta gta aaa tct gat tgc act ttg aag att ctt gac ttc ggt | | | | | | | | | | | | 531 |
| Asn Ile Val Val Lys Ser Asp Cys Thr Leu Lys Ile Leu Asp Phe Gly | | | | | | | | | | | | |
| 160 165 170 | | | | | | | | | | | | |
| ctg gcc agg act gca gga acg agt ttt atg atg acg cct tat gta gtg | | | | | | | | | | | | 579 |
| Leu Ala Arg Thr Ala Gly Thr Ser Phe Met Met Thr Pro Tyr Val Val | | | | | | | | | | | | |
| 175 180 185 | | | | | | | | | | | | |
| act cgc tac tac aga gca ccc gag gtc atc ctt ggc atg ggc tac aag | | | | | | | | | | | | 627 |
| Thr Arg Tyr Tyr Arg Ala Pro Glu Val Ile Leu Gly Met Gly Tyr Lys | | | | | | | | | | | | |
| 190 195 200 | | | | | | | | | | | | |
| gaa aac gtg gat tta tgg tct gtg ggg tgc att atg gga gaa atg gtt | | | | | | | | | | | | 675 |
| Glu Asn Val Asp Leu Trp Ser Val Gly Cys Ile Met Gly Glu Met Val | | | | | | | | | | | | |
| 205 210 215 | | | | | | | | | | | | |
| tgc cac aaa atc ctc ttt cca gga agg gac tat att gat cag tgg aat | | | | | | | | | | | | 723 |
| Cys His Lys Ile Leu Phe Pro Gly Arg Asp Tyr Ile Asp Gln Trp Asn | | | | | | | | | | | | |
| 220 225 230 235 | | | | | | | | | | | | |
| aaa gtt att gaa cag ctt gga aca cca tgt cct gaa ttc atg aag aaa | | | | | | | | | | | | 771 |
| Lys Val Ile Glu Gln Leu Gly Thr Pro Cys Pro Glu Phe Met Lys Lys | | | | | | | | | | | | |
| 240 245 250 | | | | | | | | | | | | |

| | |
|---|---|
| ctg caa cca aca gta agg act tac gtt gaa aac aga cct aaa tat gct<br>Leu Gln Pro Thr Val Arg Thr Tyr Val Glu Asn Arg Pro Lys Tyr Ala<br>              255                    260                 265 | 819 |
| gga tat agc ttt gag aaa ctc ttc cct gat gtc ctt ttc cca gct gac<br>Gly Tyr Ser Phe Glu Lys Leu Phe Pro Asp Val Leu Phe Pro Ala Asp<br>           270                    275                    280 | 867 |
| tca gaa cac aac aaa ctt aaa gcc agt cag gca agg gat ttg tta tcc<br>Ser Glu His Asn Lys Leu Lys Ala Ser Gln Ala Arg Asp Leu Leu Ser<br>285                    290                    295 | 915 |
| aaa atg ctg gta ata gat gca tct aaa agg atc tct gta gat gaa gct<br>Lys Met Leu Val Ile Asp Ala Ser Lys Arg Ile Ser Val Asp Glu Ala<br>300                    305                    310                    315 | 963 |
| ctc caa cac ccg tac atc aat gtc tgg tat gat cct tct gaa gca gaa<br>Leu Gln His Pro Tyr Ile Asn Val Trp Tyr Asp Pro Ser Glu Ala Glu<br>           320                    325                    330 | 1011 |
| gct cca cca cca aag atc cct gac aag cag tta gat gaa agg gaa cac<br>Ala Pro Pro Pro Lys Ile Pro Asp Lys Gln Leu Asp Glu Arg Glu His<br>           335                    340                    345 | 1059 |
| aca ata gaa gag tgg aaa gaa ttg ata tat aag gaa gtt atg gac ttg<br>Thr Ile Glu Glu Trp Lys Glu Leu Ile Tyr Lys Glu Val Met Asp Leu<br>        350                    355                    360 | 1107 |
| gag gag aga acc aag aat gga gtt ata cgg ggg cag ccc tct cct tta<br>Glu Glu Arg Thr Lys Asn Gly Val Ile Arg Gly Gln Pro Ser Pro Leu<br>365                    370                    375 | 1155 |
| gca cag gtg cag cag tga tcaatgctc tcagcatcca tcatcatcgt<br>Ala Gln Val Gln Gln<br>380                    385 | 1203 |
| cgtctgtcaa tgatgtgtct tcaatgtcaa cagatccgac tttggcctct gatacagaca | 1263 |
| gcagtctaga agcagcagct gggcctctgg gctgctgtag atgactactt gggccatcgg | 1323 |
| ggggtgggag ggatggggag tcggttagtc attgatagaa ctactttgaa aacaattcag | 1383 |
| tggtcttatt tttgggtgat ttttcaaaaa atgta | 1418 |

<210> SEQ ID NO 15
<211> LENGTH: 384
<212> TYPE: PRT
<213> ORGANISM: Homo sapiens

<400> SEQUENCE: 15

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

```
Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Lys
                325                 330                 335

Ile Pro Asp Lys Gln Leu Asp Glu Arg Glu His Thr Ile Glu Glu Trp
        340                 345                 350

Lys Glu Leu Ile Tyr Lys Glu Val Met Asp Leu Glu Glu Arg Thr Lys
    355                 360                 365

Asn Gly Val Ile Arg Gly Gln Pro Ser Pro Leu Ala Gln Val Gln Gln
370                 375                 380

<210> SEQ ID NO 16
<211> LENGTH: 1782
<212> TYPE: DNA
<213> ORGANISM: Homo sapiens
<220> FEATURE:
<221> NAME/KEY: CDS
<222> LOCATION: (59)..(1333)
<300> PUBLICATION INFORMATION:
<308> DATABASE ACCESSION NUMBER: L31951/Genbank
<309> DATABASE ENTRY DATE: 1994-12-06

<400> SEQUENCE: 16
gggcgggcga gggatctgaa acttgcccac ccttcgggat attgcaggac gctgcatc            58 atg agc gac agt aaa tgt gac agt cag ttt tat agt gtg caa gtg gca           106
Met Ser Asp Ser Lys Cys Asp Ser Gln Phe Tyr Ser Val Gln Val Ala
1               5                   10                  15 gac tca acc ttc act gtc cta aaa cgt tac cag cag ctg aaa cca att           154
Asp Ser Thr Phe Thr Val Leu Lys Arg Tyr Gln Gln Leu Lys Pro Ile
            20                  25                  30 ggc tct ggg gcc caa ggg att gtt tgt gct gca ttt gat aca gtt ctt           202
Gly Ser Gly Ala Gln Gly Ile Val Cys Ala Ala Phe Asp Thr Val Leu
        35                  40                  45 ggg ata agt gtt gca gtc aag aaa cta agc cgt cct ttt cag aac caa           250
Gly Ile Ser Val Ala Val Lys Lys Leu Ser Arg Pro Phe Gln Asn Gln
    50                  55                  60 act cat gca aag aga gct tat cgt gaa ctt gtc ctc tta aaa tgt gtc           298
Thr His Ala Lys Arg Ala Tyr Arg Glu Leu Val Leu Leu Lys Cys Val
```

```
                65                  70                  75                  80 aat cat aaa aat ata att agt ttg tta aat gtg ttt aca cca caa aaa        346
Asn His Lys Asn Ile Ile Ser Leu Leu Asn Val Phe Thr Pro Gln Lys
                    85                  90                  95 act cta gaa gaa ttt caa gat gtg tat ttg gtt atg gaa tta atg gat        394
Thr Leu Glu Glu Phe Gln Asp Val Tyr Leu Val Met Glu Leu Met Asp
                    100                 105                 110 gct aac tta tgt cag gtt att cac atg gag ctg gat cat gaa aga atg        442
Ala Asn Leu Cys Gln Val Ile His Met Glu Leu Asp His Glu Arg Met
                    115                 120                 125 tcc tac ctt ctt tac cag atg ctt tgt ggt att aaa cat ctg cat tca        490
Ser Tyr Leu Leu Tyr Gln Met Leu Cys Gly Ile Lys His Leu His Ser
                    130                 135                 140 gct ggt ata att cat aga gat ttg aag cct agc aac att gtt gtg aaa        538
Ala Gly Ile Ile His Arg Asp Leu Lys Pro Ser Asn Ile Val Val Lys
145                 150                 155                 160 tca gac tgc acc ctg aag atc ctt gac ttt ggc ctg gcc cgg aca gcg        586
Ser Asp Cys Thr Leu Lys Ile Leu Asp Phe Gly Leu Ala Arg Thr Ala
                    165                 170                 175 tgc act aac ttc atg atg acc cct tac gtg gtg aca cgg tac tac cgg        634
Cys Thr Asn Phe Met Met Thr Pro Tyr Val Val Thr Arg Tyr Tyr Arg
                    180                 185                 190 gcg ccc gaa gtc atc ctg ggt atg ggc tac aaa gag aac gtt gat atc        682
Ala Pro Glu Val Ile Leu Gly Met Gly Tyr Lys Glu Asn Val Asp Ile
                    195                 200                 205 tgg tca gtg ggt tgc atc atg gga gag ctg gtg aaa ggt tgt gtg ata        730
Trp Ser Val Gly Cys Ile Met Gly Glu Leu Val Lys Gly Cys Val Ile
                    210                 215                 220 ttc caa ggc act gac cat att gat cag tgg aat aaa gtt att gag cag        778
Phe Gln Gly Thr Asp His Ile Asp Gln Trp Asn Lys Val Ile Glu Gln
225                 230                 235                 240 ctg gga aca cca tca gca gag ttc atg aag aaa ctt cag cca act gtg        826
Leu Gly Thr Pro Ser Ala Glu Phe Met Lys Lys Leu Gln Pro Thr Val
                    245                 250                 255 agg aat tat gtc gaa aac aga cca aag tat cct gga atc aaa ttt gaa        874
Arg Asn Tyr Val Glu Asn Arg Pro Lys Tyr Pro Gly Ile Lys Phe Glu
                    260                 265                 270 gaa ctc ttt cca gat tgg ata ttc cca tca gaa tct gag cga gac aaa        922
Glu Leu Phe Pro Asp Trp Ile Phe Pro Ser Glu Ser Glu Arg Asp Lys
                    275                 280                 285 ata aaa aca agt caa gcc aga gat ctg tta tca aaa atg tta gtg att        970
Ile Lys Thr Ser Gln Ala Arg Asp Leu Leu Ser Lys Met Leu Val Ile
                    290                 295                 300 gat cct gac aag cgg atc tct gta gac gaa gct ctg cgt cac cca tac       1018
Asp Pro Asp Lys Arg Ile Ser Val Asp Glu Ala Leu Arg His Pro Tyr
305                 310                 315                 320 atc act gtt tgg tat gac ccc gcc gaa gca gaa gcc cca cca cct caa       1066
Ile Thr Val Trp Tyr Asp Pro Ala Glu Ala Glu Ala Pro Pro Pro Gln
                    325                 330                 335 att tat gat gcc cag ttg gaa gaa aga gaa cat gca att gaa gaa tgg       1114
Ile Tyr Asp Ala Gln Leu Glu Glu Arg Glu His Ala Ile Glu Glu Trp
                    340                 345                 350 aaa gag cta att tac aaa gaa gtc atg gat tgg gaa gaa aga agc aag       1162
Lys Glu Leu Ile Tyr Lys Glu Val Met Asp Trp Glu Glu Arg Ser Lys
                    355                 360                 365 aat ggt gtt gta aaa gat cag cct tca gat gca gca gta agt agc aac       1210
Asn Gly Val Val Lys Asp Gln Pro Ser Asp Ala Ala Val Ser Ser Asn
                    370                 375                 380 gcc act cct tct cag tct tca tcg atc aat gac att tca tcc atg tcc       1258
```

| | | | | | | | | | | | |
|---|---|---|---|---|---|---|---|---|---|---|---|
| Ala | Thr | Pro | Ser | Gln | Ser | Ser | Ile | Asn | Asp | Ile | Ser | Ser | Met | Ser |
| 385 | | | | 390 | | | | 395 | | | | 400 |

```
act gag cag acg ctg gcc tca gac aca gac agc agt ctt gat gcc tcg      1306
Thr Glu Gln Thr Leu Ala Ser Asp Thr Asp Ser Ser Leu Asp Ala Ser
            405                 410                 415 acg gga ccc ctt gaa ggc tgt cga tga taggttagaa atagcaaacc            1353
Thr Gly Pro Leu Glu Gly Cys Arg
        420                 425 tgtcagcatt gaaggaactc tcacctccgt gggcctgaaa tgcttgggag ttgatggaac    1413
caaatagaaa aactccatgt tctgcatgta agaaacacaa tgccttgccc tattcagacc    1473
tgataggatt gcctgcttag atgataaaat gaggcagaat atgtctgaag aaaaaaattg    1533
caagccacac ttctagagat tttgttcaag atcatttcag gtgagcagtt agagtaggtg    1593
aatttgtttc aaattgtact agtgacagtt tctcatcatc tgtaactgtt gagatgtatg    1653
tgcatgtgac cacaaatgct tgcttggact tgcccatcta gcactttgga aatcagtatt    1713
taaatgccaa ataatcttcc aggtagtgct gcttctgaag ttatctctta atcctcttaa    1773
gtaatttgg                                                            1782

<210> SEQ ID NO 17
<211> LENGTH: 424
<212> TYPE: PRT
<213> ORGANISM: Homo sapiens

<400> SEQUENCE: 17
```

| | | | | | | | | | | | | | | |
|---|---|---|---|---|---|---|---|---|---|---|---|---|---|---|
| Met | Ser | Asp | Ser | Lys | Cys | Asp | Ser | Gln | Phe | Tyr | Ser | Val | Gln | Val | Ala |
| 1 | | | | 5 | | | | | 10 | | | | | 15 |
| Asp | Ser | Thr | Phe | Thr | Val | Leu | Lys | Arg | Tyr | Gln | Gln | Leu | Lys | Pro | Ile |
| | | | 20 | | | | | 25 | | | | | 30 |
| Gly | Ser | Gly | Ala | Gln | Gly | Ile | Val | Cys | Ala | Ala | Phe | Asp | Thr | Val | Leu |
| | | 35 | | | | | 40 | | | | | 45 |
| Gly | Ile | Ser | Val | Ala | Val | Lys | Lys | Leu | Ser | Arg | Pro | Phe | Gln | Asn | Gln |
| 50 | | | | | 55 | | | | | 60 |
| Thr | His | Ala | Lys | Arg | Ala | Tyr | Arg | Glu | Leu | Val | Leu | Leu | Lys | Cys | Val |
| 65 | | | | | 70 | | | | | 75 | | | | | 80 |
| Asn | His | Lys | Asn | Ile | Ile | Ser | Leu | Leu | Asn | Val | Phe | Thr | Pro | Gln | Lys |
| | | | | 85 | | | | | 90 | | | | | 95 |
| Thr | Leu | Glu | Glu | Phe | Gln | Asp | Val | Tyr | Leu | Val | Met | Glu | Leu | Met | Asp |
| | | | 100 | | | | | 105 | | | | | 110 |
| Ala | Asn | Leu | Cys | Gln | Val | Ile | His | Met | Glu | Leu | Asp | His | Glu | Arg | Met |
| | | 115 | | | | | 120 | | | | | 125 |
| Ser | Tyr | Leu | Leu | Tyr | Gln | Met | Leu | Cys | Gly | Ile | Lys | His | Leu | His | Ser |
| | 130 | | | | | 135 | | | | | 140 |
| Ala | Gly | Ile | Ile | His | Arg | Asp | Leu | Lys | Pro | Ser | Asn | Ile | Val | Val | Lys |
| 145 | | | | | 150 | | | | | 155 | | | | | 160 |
| Ser | Asp | Cys | Thr | Leu | Lys | Ile | Leu | Asp | Phe | Gly | Leu | Ala | Arg | Thr | Ala |
| | | | 165 | | | | | 170 | | | | | 175 |
| Cys | Thr | Asn | Phe | Met | Met | Thr | Pro | Tyr | Val | Val | Thr | Arg | Tyr | Tyr | Arg |
| | | | 180 | | | | | 185 | | | | | 190 |
| Ala | Pro | Glu | Val | Ile | Leu | Gly | Met | Gly | Tyr | Lys | Glu | Asn | Val | Asp | Ile |
| | | 195 | | | | | 200 | | | | | 205 |
| Trp | Ser | Val | Gly | Cys | Ile | Met | Gly | Glu | Leu | Val | Lys | Gly | Cys | Val | Ile |
| | 210 | | | | | 215 | | | | | 220 |
| Phe | Gln | Gly | Thr | Asp | His | Ile | Asp | Gln | Trp | Asn | Lys | Val | Ile | Glu | Gln |
| 225 | | | | | 230 | | | | | 235 | | | | | 240 |

```
Leu Gly Thr Pro Ser Ala Glu Phe Met Lys Lys Leu Gln Pro Thr Val
            245                 250                 255

Arg Asn Tyr Val Glu Asn Arg Pro Lys Tyr Pro Gly Ile Lys Phe Glu
        260                 265                 270

Glu Leu Phe Pro Asp Trp Ile Phe Pro Ser Glu Ser Glu Arg Asp Lys
    275                 280                 285

Ile Lys Thr Ser Gln Ala Arg Asp Leu Leu Ser Lys Met Leu Val Ile
290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
        355                 360                 365

Asn Gly Val Val Lys Asp Gln Pro Ser Asp Ala Ala Val Ser Ser Asn
370                 375                 380

Ala Thr Pro Ser Gln Ser Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420

<210> SEQ ID NO 18
<211> LENGTH: 3834
<212> TYPE: DNA
<213> ORGANISM: Homo sapiens
<220> FEATURE:
<221> NAME/KEY: CDS
<222> LOCATION: (117)..(1949)
<300> PUBLICATION INFORMATION:
<308> DATABASE ACCESSION NUMBER: M24736/Genbank
<309> DATABASE ENTRY DATE: 1994-11-07

<400> SEQUENCE: 18
cctgagacag aggcagcagt gatacccacc tgagagatcc tgtgtttgaa caactgcttc        60
ccaaaacgga agtatttca agcctaaacc tttgggtgaa agaactctt gaagtc atg        119
                                                              Met
                                                                1 att gct tca cag ttt ctc tca gct ctc act ttg gtg ctt ctc att aaa        167
Ile Ala Ser Gln Phe Leu Ser Ala Leu Thr Leu Val Leu Leu Ile Lys
        5                   10                  15 gag agt gga gcc tgg tct tac aac acc tcc acg gaa gct atg act tat        215
Glu Ser Gly Ala Trp Ser Tyr Asn Thr Ser Thr Glu Ala Met Thr Tyr
    20                  25                  30 gat gag gcc agt gct tat tgt cag caa agg tac aca cac ctg gtt gca        263
Asp Glu Ala Ser Ala Tyr Cys Gln Gln Arg Tyr Thr His Leu Val Ala
35                  40                  45 att caa aac aaa gaa gag att gag tac cta aac tcc ata ttg agc tat        311
Ile Gln Asn Lys Glu Glu Ile Glu Tyr Leu Asn Ser Ile Leu Ser Tyr
50                  55                  60                  65 tca cca agt tat tac tgg att gga atc aga aaa gtc aac aat gtg tgg        359
Ser Pro Ser Tyr Tyr Trp Ile Gly Ile Arg Lys Val Asn Asn Val Trp
            70                  75                  80 gtc tgg gta gga acc cag aaa cct ctg aca gaa gaa gcc aag aac tgg        407
Val Trp Val Gly Thr Gln Lys Pro Leu Thr Glu Glu Ala Lys Asn Trp
```

-continued

|  |  |  | 85 |  |  |  | 90 |  |  |  | 95 |  |  |  |
|---|---|---|---|---|---|---|---|---|---|---|---|---|---|---|
| gct | cca | ggt | gaa | ccc | aac | aat | agg | caa | aaa | gat | gag | gac | tgc | gtg gag |
| Ala | Pro | Gly | Glu | Pro | Asn | Asn | Arg | Gln | Lys | Asp | Glu | Asp | Cys | Val Glu |
|  |  | 100 |  |  |  | 105 |  |  |  | 110 |  |  |  |  |

455 atc tac atc aag aga gaa aaa gat gtg ggc atg tgg aat gat gag agg    503
Ile Tyr Ile Lys Arg Glu Lys Asp Val Gly Met Trp Asn Asp Glu Arg
    115             120             125 tgc agc aag aag aag ctt gcc cta tgc tac aca gct gcc tgt acc aat    551
Cys Ser Lys Lys Lys Leu Ala Leu Cys Tyr Thr Ala Ala Cys Thr Asn
130             135             140             145 aca tcc tgc agt ggc cac ggt gaa tgt gta gag acc atc aat aat tac    599
Thr Ser Cys Ser Gly His Gly Glu Cys Val Glu Thr Ile Asn Asn Tyr
            150             155             160 act tgc aag tgt gac cct ggc ttc agt gga ctc aag tgt gag caa att    647
Thr Cys Lys Cys Asp Pro Gly Phe Ser Gly Leu Lys Cys Glu Gln Ile
            165             170             175 gtg aac tgt aca gcc ctg gaa tcc cct gag cat gga agc ctg gtt tgc    695
Val Asn Cys Thr Ala Leu Glu Ser Pro Glu His Gly Ser Leu Val Cys
        180             185             190 agt cac cca ctg gga aac ttc agc tac aat tct tcc tgc tct atc agc    743
Ser His Pro Leu Gly Asn Phe Ser Tyr Asn Ser Ser Cys Ser Ile Ser
    195             200             205 tgt gat agg ggt tac ctg cca agc agc atg gag acc atg cag tgt atg    791
Cys Asp Arg Gly Tyr Leu Pro Ser Ser Met Glu Thr Met Gln Cys Met
210             215             220             225 tcc tct gga gaa tgg agt gct cct att cca gcc tgc aat gtg gtt gag    839
Ser Ser Gly Glu Trp Ser Ala Pro Ile Pro Ala Cys Asn Val Val Glu
            230             235             240 tgt gat gct gtg aca aat cca gcc aat ggg ttc gtg gaa tgt ttc caa    887
Cys Asp Ala Val Thr Asn Pro Ala Asn Gly Phe Val Glu Cys Phe Gln
            245             250             255 aac cct gga agc ttc cca tgg aac aca acc tgt aca ttt gac tgt gaa    935
Asn Pro Gly Ser Phe Pro Trp Asn Thr Thr Cys Thr Phe Asp Cys Glu
    260             265             270 gaa gga ttt gaa cta atg gga gcc cag agc ctt cag tgt acc tca tct    983
Glu Gly Phe Glu Leu Met Gly Ala Gln Ser Leu Gln Cys Thr Ser Ser
    275             280             285 ggg aat tgg gac aac gag aag cca acg tgt aaa gct gtg aca tgc agg    1031
Gly Asn Trp Asp Asn Glu Lys Pro Thr Cys Lys Ala Val Thr Cys Arg
290             295             300             305 gcc gtc cgc cag cct cag aat ggc tct gtg agg tgc agc cat tcc cct    1079
Ala Val Arg Gln Pro Gln Asn Gly Ser Val Arg Cys Ser His Ser Pro
            310             315             320 gct gga gag ttc acc ttc aaa tca tcc tgc aac ttc acc tgt gag gaa    1127
Ala Gly Glu Phe Thr Phe Lys Ser Ser Cys Asn Phe Thr Cys Glu Glu
        325             330             335 ggc ttc atg ttg cag gga cca gcc cag gtt gaa tgc acc act caa ggg    1175
Gly Phe Met Leu Gln Gly Pro Ala Gln Val Glu Cys Thr Thr Gln Gly
    340             345             350 cag tgg aca cag caa atc cca gtt tgt gaa gct ttc cag tgc aca gcc    1223
Gln Trp Thr Gln Gln Ile Pro Val Cys Glu Ala Phe Gln Cys Thr Ala
    355             360             365 ttg tcc aac ccc gag cga ggc tac atg aat tgt ctt cct agt gct tct    1271
Leu Ser Asn Pro Glu Arg Gly Tyr Met Asn Cys Leu Pro Ser Ala Ser
370             375             380             385 ggc agt ttc cgt tat ggg tcc agc tgt gag ttc tcc tgt gag cag ggt    1319
Gly Ser Phe Arg Tyr Gly Ser Ser Cys Glu Phe Ser Cys Glu Gln Gly
            390             395             400 ttt gtg ttg aag gga tcc aaa agg ctc caa tgt ggc ccc aca ggg gag    1367

```
                          -continued

Phe Val Leu Lys Gly Ser Lys Arg Leu Gln Cys Gly Pro Thr Gly Glu
            405                 410                 415 tgg gac aac gag aag ccc aca tgt gaa gct gtg aga tgc gat gct gtc     1415
Trp Asp Asn Glu Lys Pro Thr Cys Glu Ala Val Arg Cys Asp Ala Val
        420                 425                 430 cac cag ccc ccg aag ggt ttg gtg agg tgt gct cat tcc cct att gga     1463
His Gln Pro Pro Lys Gly Leu Val Arg Cys Ala His Ser Pro Ile Gly
435                 440                 445 gaa ttc acc tac aag tcc tct tgt gcc ttc agc tgt gag gag gga ttt     1511
Glu Phe Thr Tyr Lys Ser Ser Cys Ala Phe Ser Cys Glu Glu Gly Phe
450                 455                 460                 465 gaa tta tat gga tca act caa ctt gag tgc aca tct cag gga caa tgg     1559
Glu Leu Tyr Gly Ser Thr Gln Leu Glu Cys Thr Ser Gln Gly Gln Trp
                470                 475                 480 aca gaa gag gtt cct tcc tgc caa gtg gta aaa tgt tca agc ctg gca     1607
Thr Glu Glu Val Pro Ser Cys Gln Val Val Lys Cys Ser Ser Leu Ala
            485                 490                 495 gtt ccg gga aag atc aac atg agc tgc agt ggg gag ccc gtg ttt ggc     1655
Val Pro Gly Lys Ile Asn Met Ser Cys Ser Gly Glu Pro Val Phe Gly
        500                 505                 510 act gtg tgc aag ttc gcc tgt cct gaa gga tgg acg ctc aat ggc tct     1703
Thr Val Cys Lys Phe Ala Cys Pro Glu Gly Trp Thr Leu Asn Gly Ser
515                 520                 525 gca gct cgg aca tgt gga gcc aca gga cac tgg tct ggc ctg cta cct     1751
Ala Ala Arg Thr Cys Gly Ala Thr Gly His Trp Ser Gly Leu Leu Pro
530                 535                 540                 545 acc tgt gaa gct ccc act gag tcc aac att ccc ttg gta gct gga ctt     1799
Thr Cys Glu Ala Pro Thr Glu Ser Asn Ile Pro Leu Val Ala Gly Leu
                550                 555                 560 tct gct gct gga ctc tcc ctc ctg aca tta gca cca ttt ctc ctc tgg     1847
Ser Ala Ala Gly Leu Ser Leu Leu Thr Leu Ala Pro Phe Leu Leu Trp
            565                 570                 575 ctt cgg aaa tgc tta cgg aaa gca aag aaa ttt gtt cct gcc agc agc     1895
Leu Arg Lys Cys Leu Arg Lys Ala Lys Lys Phe Val Pro Ala Ser Ser
        580                 585                 590 tgc caa agc ctt gaa tca gac gga agc tac caa aag cct tct tac atc     1943
Cys Gln Ser Leu Glu Ser Asp Gly Ser Tyr Gln Lys Pro Ser Tyr Ile
595                 600                 605 ctt taa gttcaaaaga atcagaaaca ggtgcatctg ggaactaga gggatacact      1999
Leu
610 gaagttaaca gagacagata actctcctcg ggtctctggc ccttcttgcc tactatgcca   2059 gatgccttta tggctgaaac cgcaacaccc atcaccactt caatagatca agtccagca   2119 ggcaaggacg gccttcaact gaaaagactc agtgttccct ttcctactct caggatcaag  2179 aaagtgttgg ctaatgaagg gaaaggatat tttcttccaa gcaaaggtga agagaccaag  2239 actctgaaat ctcagaattc cttttctaac tctcccttgc tcgctgtaaa atcttggcac  2299 agaaacacaa tattttgtgg ctttctttct tttgcccttc acagtgtttc gacagctgat  2359 tacacagttg ctgtcataag aatgaataat aattatccag agtttagagg aaaaaaatga  2419 ctaaaaatat tataacttaa aaaatgaca gatgttgaat gcccacaggc aaatgcatgg   2479 agggttgtta atggtgcaaa tcctactgaa tgctctgtgc gagggttact atgcacaatt  2539 taatcacttt catccctatg ggattcagtg cttcttaaag agttcttaag gattgtgata  2599 tttttacttg cattgaatat attataatct tccatacttc ttcattcaat acaagtgtgg  2659 tagggactta aaaaacttgt aaatgctgtc aactatgata tggtaaaagt tacttattct  2719
```

-continued

```
agattacccc ctcattgttt attaacaaat tatgttacat ctgttttaaa tttatttcaa    2779
aaagggaaac tattgtcccc tagcaaggca tgatgttaac cagaataaag ttctgagtgt    2839
ttttactaca gttgtttttt gaaacatgg tagaattgga gagtaaaaac tgaatggaag    2899
gtttgtatat tgtcagatat ttttcagaa atatgtggtt tccacgatga aaacttcca    2959 tgaggccaaa cgttttgaac taataaaagc ataaatgcaa acacacaaag gtataatttt    3019
atgaatgtct tgttggaaa agaatacaga aagatggatg tgctttgcat tcctacaaag    3079
atgtttgtca gatgtgatat gtaaacataa ttcttgtata ttatggaaga ttttaaattc    3139
acaatagaaa ctcaccatgt aaaagagtca tctggtagat ttttaacgaa tgaagatgtc    3199
taatagttat tccctatttg ttttcttctg tatgttaggg tgctctggaa gagaggaatg    3259
cctgtgtgag caagcattta tgtttattta aagcagatt taacaattcc aaaggaatct    3319
ccagttttca gttgatcact ggcaatgaaa aattctcagt cagtaattgc caaagctgct    3379
ctagccttga ggagtgtgag aatcaaaact ctcctacact tccattaact tagcatgtgt    3439
tgaaaaaaaa agtttcagag aagttctggc tgaacactgg caacgacaaa gccaacagtc    3499
aaaacagaga tgtgataagg atcagaacag cagaggttct tttaaagggg cagaaaaact    3559
ctgggaaata agagagaaca actactgtga tcaggctatg tatggaatac agtgttattt    3619
tctttgaaat tgtttaagtg ttgtaaatat ttatgtaaac tgcattagaa attagctgtg    3679
tgaaatacca gtgtggtttg tgtttgagtt ttattgagaa ttttaaatta aacttaaaa    3739 tattttataa ttttaaagt atatatttat ttaagcttat gtcagaccta tttgacataa    3799
cactataaag gttgacaata aatgtgctta tgttt    3834
```

<210> SEQ ID NO 19
<211> LENGTH: 610
<212> TYPE: PRT
<213> ORGANISM: Homo sapiens

<400> SEQUENCE: 19

```
Met Ile Ala Ser Gln Phe Leu Ser Ala Leu Thr Leu Val Leu Leu Ile
 1               5                  10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Lys Leu Ala Leu Cys Tyr Thr Ala Ala Cys Thr
    130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175
```

-continued

```
Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
            195                 200                 205

Ser Cys Asp Arg Gly Tyr Leu Pro Ser Ser Met Glu Thr Met Gln Cys
            210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
            275                 280                 285

Ser Gly Asn Trp Asp Asn Glu Lys Pro Thr Cys Lys Ala Val Thr Cys
            290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
            355                 360                 365

Ala Leu Ser Asn Pro Glu Arg Gly Tyr Met Asn Cys Leu Pro Ser Ala
            370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
                405                 410                 415

Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
            435                 440                 445

Gly Glu Phe Thr Tyr Lys Ser Ser Cys Ala Phe Ser Cys Glu Glu Gly
            450                 455                 460

Phe Glu Leu Tyr Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
            515                 520                 525

Ser Ala Ala Arg Thr Cys Gly Ala Thr Gly His Trp Ser Gly Leu Leu
            530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
```

```
                    595                 600                 605
Ile Leu
    610
```

`<210> SEQ ID NO 20`
`<211> LENGTH: 25`
`<212> TYPE: DNA`
`<213> ORGANISM: Artificial Sequence`
`<220> FEATURE:`
`<223> OTHER INFORMATION: PCR primer`

`<400> SEQUENCE: 20`

`ttgaagtcat gattgcttca cagtt                                          25`

`<210> SEQ ID NO 21`
`<211> LENGTH: 26`
`<212> TYPE: DNA`
`<213> ORGANISM: Artificial Sequence`
`<220> FEATURE:`
`<223> OTHER INFORMATION: PCR primer`

`<400> SEQUENCE: 21`

`ttctgattct tttgaactta aaggat                                         26`

`<210> SEQ ID NO 22`
`<211> LENGTH: 23`
`<212> TYPE: DNA`
`<213> ORGANISM: Artificial Sequence`
`<220> FEATURE:`
`<223> OTHER INFORMATION: PCR primer`

`<400> SEQUENCE: 22`

`cgcggatccg cgtactcaga gtt                                            23`

`<210> SEQ ID NO 23`
`<211> LENGTH: 23`
`<212> TYPE: DNA`
`<213> ORGANISM: Artificial Sequence`
`<220> FEATURE:`
`<223> OTHER INFORMATION: PCR primer`

`<400> SEQUENCE: 23`

`cggaattccg ttcagggagg cgt                                            23`

`<210> SEQ ID NO 24`
`<211> LENGTH: 26`
`<212> TYPE: DNA`
`<213> ORGANISM: Artificial Sequence`
`<220> FEATURE:`
`<223> OTHER INFORMATION: PCR primer`

`<400> SEQUENCE: 24`

`cttaaaatgc ctgggaagat ggtcgt                                         26`

`<210> SEQ ID NO 25`
`<211> LENGTH: 26`
`<212> TYPE: DNA`
`<213> ORGANISM: Artificial Sequence`
`<220> FEATURE:`
`<223> OTHER INFORMATION: PCR primer`

`<400> SEQUENCE: 25`

`atcaagcatt agctacactt ttgatt                                         26`

What is claimed is:

1. A method of modulating cell adhesion molecule expression comprising treating a cell or tissue expressing a cell adhesion molecule in vitro or ex vivo with a specific inhibitor of a Tumor Necrosis Factor alpha signaling molecule selected from the group consisting of Ha-ras and c-raf, such that cell adhesion molecule expression is modulated.

2. The method of claim 1 wherein said cell adhesion molecule is E-selectin, VCAM-1 or ICAM-1.

3. The method of claim 1 wherein said inhibitor is an antisense oligonucleotide specifically hybridizable with a nucleic acid encoding Tumor Necrosis Factor alpha signaling molecule.

4. The method of claim 3 wherein said Tumor Necrosis Factor alpha signaling molecule is Ha-ras or c-raf.

5. The method of claim 4 wherein said antisense oligonucleotide is specifically hybridizable to Ha-ras or c-raf.

6. The method of claim 5 wherein said antisense oligonucleotide has a sequence comprising SEQ ID NO. 2 or SEQ ID NO. 4.

7. The method of claim 6 wherein said antisense oligonucleotide has at least one phosphorothioate internucleotide linkage.

8. The method of claim 6 wherein said antisense oligonucleotide has at least one 2'-methoxyethoxy nucleotide.

* * * * *